US008956669B2

(12) United States Patent
Bej

(10) Patent No.: US 8,956,669 B2
(45) Date of Patent: Feb. 17, 2015

(54) ANTICANCER AND ANTIMICROBIAL COMPOUNDS FROM ANTARCTIC EXTREMOPHILIC MICROORGANSIMS

(75) Inventor: Asim Bej, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 451 days.

(21) Appl. No.: 13/202,328

(22) PCT Filed: Feb. 19, 2010

(86) PCT No.: PCT/US2010/024823
§ 371 (c)(1),
(2), (4) Date: Aug. 19, 2011

(87) PCT Pub. No.: WO2010/096719
PCT Pub. Date: Aug. 26, 2010

(65) Prior Publication Data
US 2011/0301216 A1  Dec. 8, 2011

Related U.S. Application Data

(60) Provisional application No. 61/153,882, filed on Feb. 19, 2009.

(51) Int. Cl.
| | | |
|---|---|---|
| A01N 63/00 | (2006.01) | |
| A61K 35/00 | (2006.01) | |
| A61K 31/085 | (2006.01) | |
| A61K 31/404 | (2006.01) | |

(52) U.S. Cl.
CPC ............. *A61K 31/085* (2013.01); *A61K 31/404* (2013.01)
USPC .......................................... 424/780; 424/93.4

(58) Field of Classification Search
CPC combination set(s) only.
See application file for complete search history.

(56) References Cited

U.S. PATENT DOCUMENTS

2004/0053375 A1*  3/2004  Tan et al. ...................... 435/118

OTHER PUBLICATIONS

Pantanella et al. Journal of Applied Microbiology, vol. 102, 2007, pp. 992-999.*

* cited by examiner

*Primary Examiner* — Chris R Tate
*Assistant Examiner* — Douglas F White
(74) *Attorney, Agent, or Firm* — Bradley Arant Boult Cummings, LLP

(57) ABSTRACT

The present disclosure describes the isolation of extremophilic microorganisms from the Lakes of Schirmacher Oasis located in the East Antarctic Dronning Maud Land. The isolated organisms were characterized and certain pigments produced by these microorganisms were isolated. The present disclosure teaches that the isolated pigments exhibit anticancer and antimicrobial properties and can be used as new therapies for the treatment and prevention of cancer and microbially-mediated diseases.

4 Claims, 21 Drawing Sheets

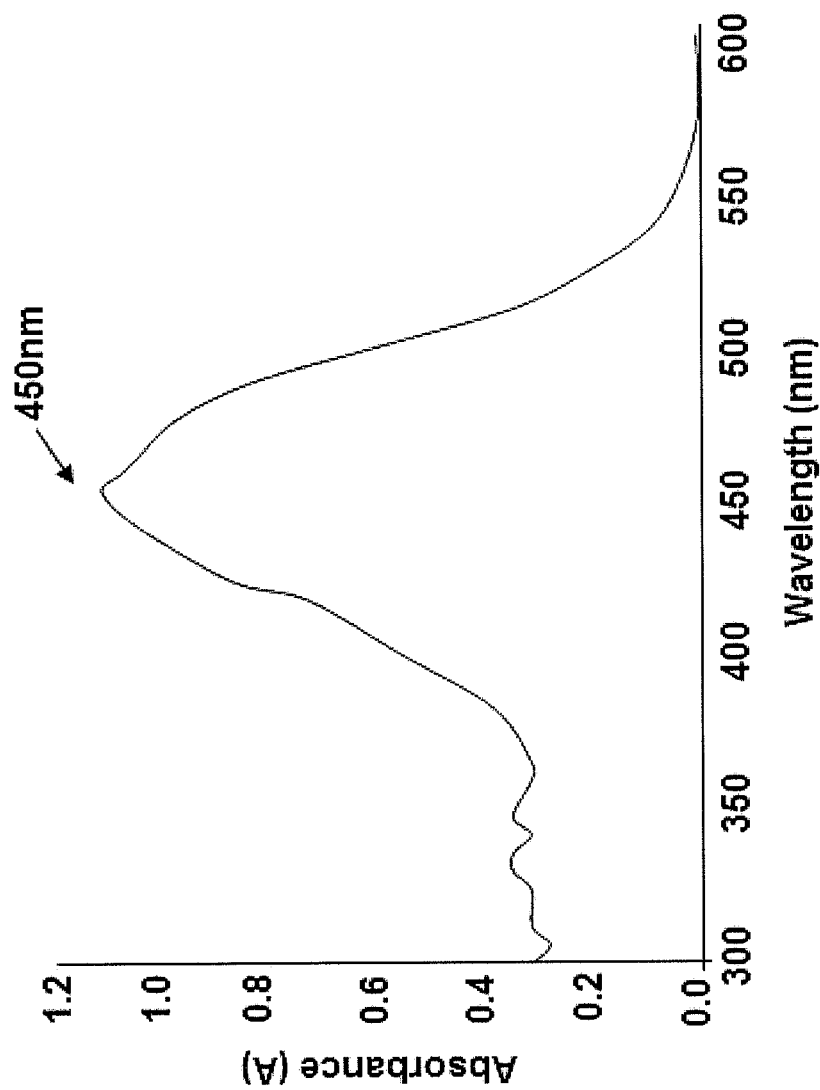

FIG. 5A

GGTTACCTTGTTACGACTTCACCCCAGTCACGAATCCTACCGTGGTAAGCGCCCTCCTTGCGG
TTAAGCTACCTACTTCTGGTAAAACCCGCTCCCATGGTGTGACGGGCGGTGTGTACAAGACCC
GGGAACGTATTCACCGCGACATGCTGATCCGCGATTACTAGCGATTCCAACTTCATGCAGTCG
AGTTGCAGACTACAATCCGGACTACGATACACTTTCTGCGATTAGCTCCCCCTCGCGGGTTGG
CGGCGCTCTGTATGTACCATTGTATGACGTGTGAAGCCCTACCCATAAGGGCCATGAGGACTT
GACGTCATCCCCACCTTCCTCCGGTTTGTCACCGGCAGTCTCATTAGAGTGCCCTTTCGTAGCA
ACTAATGACAAGGGTTGCGCTCGTTGCGGGACTTAACCCAACATCTCACGACACGAGCTGAC
GACAGCCATGCAGCACCTGTGTACTGGTTCTCTTTCGAGCACTCCCTGATCTCTCAAGGATTC
CAGCCATGTCAAGGGTAGGTAAGGTTTTTCGCGTTGCATCGAATTAATCCACATCATCCACCG
CTTGTGCGGGTCCCCGTCAATTCCTTTGAGTTTTAATCTTGCGACCGTACTCCCCAGGCGGTCT
ACTTCACGCGTTAGCTGCGGTACCAAGTCAATTAAGACCCGACAACTAGTAGACATCGTTTAG
GGCGTGGACTACCAGGGTATCTAATCCTGTTTGCTCCCCACGCTTTCGTGCATGAGCGTCAAT
CTTGACCCAGGGGGCTGCCTTCGCCATCGGTGTTCCTCCACATATCTACGCATTTCACTGCTAC
ACGTGGAATTCTACCCCCCTCTGCCAGATTCTAGCCTTGCAGTCTCCAATGCAATTCCCAGGTT
GAGCCCGGGGATTTCACATCAGACCTACAAAACCGCCTGCGCACGCTTTACGCCCAGTAATTC
CGATTAACGCTTGCACCCTACGTATTACCGCGGCTGCTGGCACGTAGTTAGCCGGTGCTTATT
CTTCAGGTACCGTCATTAGCAAGAGATATTAGCTCTCACCGTTTCTTCCCTGACAAAAGAGCT
TTACAACCCGAAGGCCTTCTTCACTCACGCGGCATTGCTGGATCAGGCTTTCGCCCATTGTCC
AAAATTCCCCACTGCTGCCTCCCGTAGGAGTCTGGACCGTGTCTCAGTTCCAGTGTGGCTGGT
CGTCCTCTCAGACCAGCTACTGATCGATGCCTTGGTAGGCTTTTACCCTACCAACTAGCTAAT
CAGATATCGGCCGCTCCACGAGCATGAGGTCTTGCGATCCCCCACTTTCATCCTTAGATCGTA
TGCGGTATTAGCGTAACTTTCGCTACGTTATCCCCCACTCTAGGGTACGTTCCGATATATTACT
CACCCGTTCGCCACTCGCCACCAGAGCAAGCTCCGTGCTGCCGTTCGACTTGCATGTGTAAGG
CATGCCGCCAGCGTTCAATCTGAGCCATGATCAAACTCT

FIG. 5B

AGAGTTTGATCATGGCTCAGGATGAACGCTAGCGGCAGGCTTAACACATGCAAGTCGAGGGG
TATGCTTCTTCGGAAGCAGAGACCGGCGCACGGGTGCGTAACGCGTATGCAATCTACCTTTTA
CAGAGGGATAGCCCAGAGAAATTTGGATTAATACCTCATAGTATATAGACCTGGCATCAGGA
TTATATTAAAGTCACAACGGTAAAAGATGAGCATGCGTCCCATTAGCTAGTTGGTAAGGTAA
CGGCTTACCAAGGCTACGATGGGTAGGGGTCCTGAGAGGGAGATCCCCCACACTGGTACTGA
GACACGGACCAGACTCCTACGGGAGGCAGCAGTGAGGAATATTGGACAATGGGCGCAAGCC
TGATCCAGCCATGCCGCGTGCAGGATGACGGTCCTATGGATTGTAAACTGCTTTTGTACAGGA
AGAAACACTGGTTCGTGAACCAGCTTGACGGTACTGTAAGAATAAGGATCGGCTAACTCCGT
GCCAGCAGCCGCGGTAATACGGAGGATCCAAGCGTTATCCGGAATCATTGGGTTTAAAGGGT
CCGTAGGCGGTTTAGTAAGTCAGTGGTGAAAGCCCATCGCTCAACGGTGGAACGGCCATTGA
TACTGCTAAACTTGAATTATTAGGAAGTAACTAGAATATGTAGTGTAGCGGTGAAATGCTTAG
AGATTACATGGAATACCAATTGCGAAGGCAGGTTACTACTAATGGATTGACGCTGATGGACG
AAAGCGTGGGTAGCGAACAGGATTAGATACCCTGGTAGTCCACGCCGTAAACGATGGATACT
AGCTGTTGGAAGCAATTTCAGTGGCTAAGCCAAAGTGATAAGTATCCCACCTGGGGAGTACG
TTCGCAAGAATGAAACTCAAAGGAATTGACGGGGGCCCGCACAAGCGGTGGAGCATGTGGTT
TAATTCGATGATACGCGAGGAACCTTACCAAGGCTTAAATGTAGATTGACCGTTTTGGAAACA
GAACTTTCGCAAGACAATTTACAAGGTGCTGCATGGTTGTCGTCAGCTCGTGCCGTGAGGTGT
CAGGTTAAGTCCTATAACGAGCGCAACCCCTGTTGTTAGTTGCCAGCGAGTCAAGTCGGGAA
CTCTAACAAGACTGCCAGTGCAAACTGTGAGGAAGGTGGGGATGACGTCAAATCATCACGGC
CCTTACGCCTTGGGCTACACACGTGCTACAATGGCCGGTACAGAGAGCAGCCACTGGGCGAC
CAGGAGCGAATCTATAAAACCGGTCACAGTTCGGATCGGAGTCTGCAACTCGACTCCGTGAA
GCTGGAATCGCTAGTAATCGGATATCAGCCATGATCCGGTGAATACGTTCCCGGGCCTTGTAC
ACACCGCCCGTCAAGCCATGGAAGCTGGGGGTGCCTGAAGTCGGTGACCCAAGGAGCTGCCT
AGGGTAAAACTGGTAACTAGGGCTAAGTCGTAACAAGGTAACC

FIG. 8D
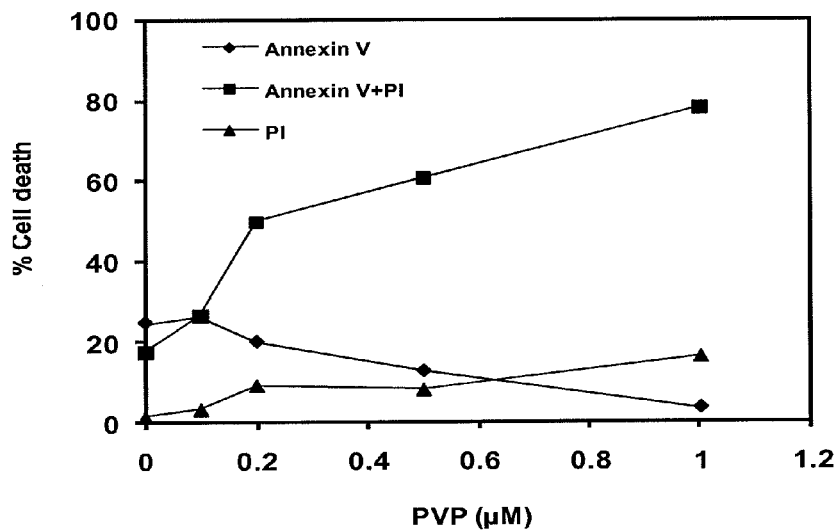
FIG. 9A
FIG. 9B
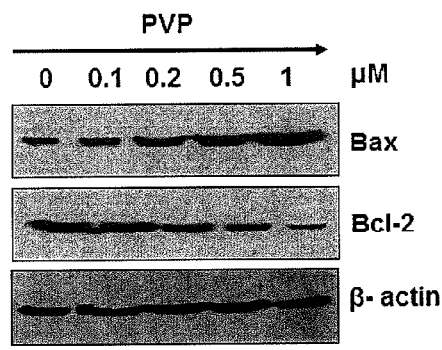
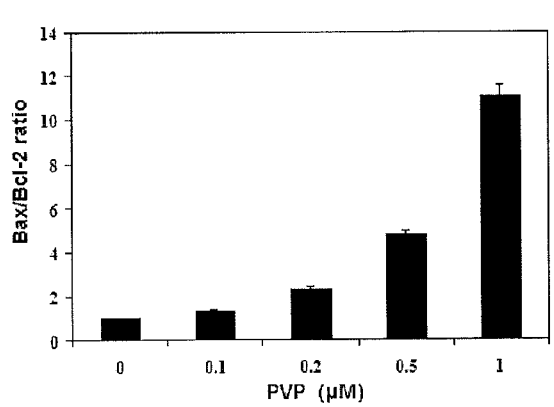

FIG. 11A
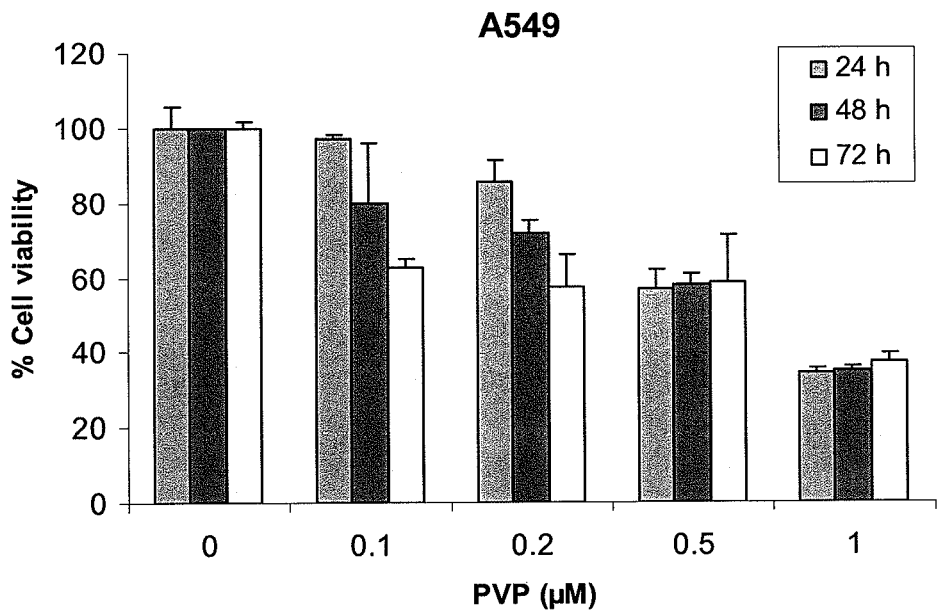
FIG. 11.B
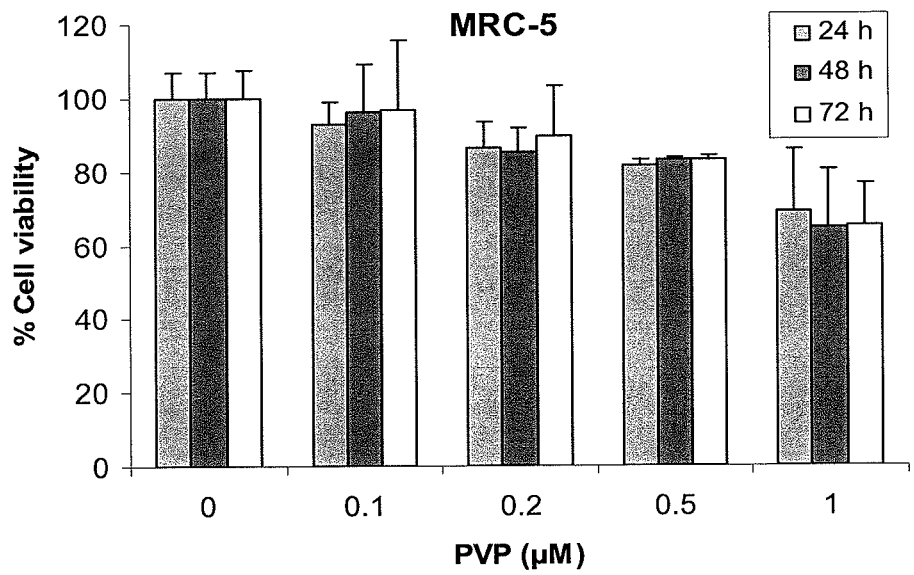

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer for 16s RNA

<400> SEQUENCE: 1
agagtttgat cctggctcag                    20

<210> SEQ ID NO 2
<211> LENGTH: 20
<212> TYPE: DNA
<213> ORGANISM: Artificial Sequence
<220> FEATURE:
<223> OTHER INFORMATION: primer for 16s RNA

<400> SEQUENCE: 2
aaggaggtaa tccagccgca                    20

<210> SEQ ID NO 3
<211> LENGTH: 1492
<212> TYPE: DNA
<213> ORGANISM: Janthinobacterium sp

<400> SEQUENCE: 3
ggttaccttg ttacgacttc accccagtca cgaatcctac cgtggtaagc gccctccttg     60
cggttaagct acctacttct ggtaaaaccc gctcccatgg tgtgacgggc ggtgtgtaca    120
agacccggga acgtattcac cgcgacatgc tgatccgcga ttactagcga ttccaacttc    180
atgcagtcga gttgcagact acaatccgga ctacgataca ctttctgcga ttagctcccc    240
ctcgcgggtt ggcggcgctc tgtatgtacc attgtatgac gtgtgaagcc ctacccataa    300
gggccatgag gacttgacgt catccccacc ttcctccggt ttgtcaccgg cagtctcatt    360
agagtgccct ttcgtagcaa ctaatgacaa gggttgcgct cgttgcggga cttaacccaa    420
catctcacga cacgagctga cgacagccat gcagcacctg tgtactggtt ctctttcgag    480
cactccctga tctctcaagg attccagcca tgtcaagggt aggtaaggtt tttcgcgttg    540
catcgaatta atccacatca tccaccgctt gtgcgggtcc ccgtcaattc ctttgagttt    600

-continued

```
taatcttgcg accgtactcc ccaggcggtc tacttcacgc gttagctgcg gtaccaagtc    660
aattaagacc cgacaactag tagacatcgt ttagggcgtg gactaccagg gtatctaatc    720
ctgtttgctc cccacgcttt cgtgcatgag cgtcaatctt gacccagggg gctgccttcg    780
ccatcggtgt tcctccacat atctacgcat ttcactgcta cacgtggaat tctacccccc    840
tctgccagat tctagccttg cagtctccaa tgcaattccc aggttgagcc cggggatttc    900
acatcagacc tacaaaaccg cctgcgcacg ctttacgccc agtaattccg attaacgctt    960
gcaccctacg tattaccgcg gctgctggca cgtagttagc cggtgcttat tcttcaggta   1020
ccgtcattag caagagatat tagctctcac cgtttcttcc ctgacaaaag gctttacaa    1080 cccgaaggcc ttcttcactc acgcggcatt gctggatcag gctttcgccc attgtccaaa   1140
attccccact gctgcctccc gtaggagtct ggaccgtgtc tcagttccag tgtggctggt   1200
cgtcctctca gaccagctac tgatcgatgc cttggtaggc ttttaccccta ccaactagct   1260 aatcagatat cggccgctcc acgagcatga ggtcttgcga tcccccactt tcatccttag   1320
atcgtatgcg gtattagcgt aactttcgct acgttatccc ccactctagg gtacgttccg   1380
atatattact cacccgttcg ccactcgcca ccagagcaag ctccgtgctg ccgttcgact   1440
tgcatgtgta aggcatgccg ccagcgttca atctgagcca tgatcaaact ct          1492
```

<210> SEQ ID NO 4
<211> LENGTH: 1475
<212> TYPE: DNA
<213> ORGANISM: Flavobacterium sp

<400> SEQUENCE: 4

```
agagtttgat catggctcag gatgaacgct agcggcaggc ttaacacatg caagtcgagg    60
ggtatgcttc ttcggaagca gagaccggcg cacgggtgcg taacgcgtat gcaatctacc   120
ttttacagag ggatagccca gagaaatttg gattaatacc tcatagtata tagacctggc   180
atcaggatta tattaaagtc acaacggtaa aagatgagca tgcgtcccat tagctagttg   240
gtaaggtaac ggcttaccaa ggctacgatg ggtaggggtc ctgagaggga gatccccac    300 actggtactg agacacggac cagactccta cgggaggcag cagtgaggaa tattggacaa   360
tgggcgcaag cctgatccag ccatgccgcg tgcaggatga cggtcctatg gattgtaaac   420
tgcttttgta caggaagaaa cactggttcg tgaaccagct tgacggtact gtaagaataa   480
ggatcggcta actccgtgcc agcagccgcg gtaatacgga ggatccaagc gttatccgga   540
atcattgggt ttaaagggtc cgtaggcggt ttagtaagtc agtggtgaaa gcccatcgct   600
caacggtgga acggccattg atactgctaa acttgaatta ttaggaagta actagaatat   660
gtagtgtagc ggtgaaatgc ttagagatta catggaatac caattgcgaa ggcaggttac   720
tactaatgga ttgacgctga tggacgaaag cgtgggtagc gaacaggatt agataccctg   780
gtagtccacg ccgtaaacga tggatactag ctgttggaag caatttcagt ggctaagcca   840
aagtgataag tatcccacct ggggagtacg ttcgcaagaa tgaaactcaa aggaattgac   900
gggggcccgc acaagcggtg gagcatgtgg tttaattcga tgatacgcga ggaaccttac   960
caaggcttaa atgtagattg accgtttgg aaacagaact ttcgcaagac aatttacaag   1020
gtgctgcatg gttgtcgtca gctcgtgccg tgaggtgtca ggttaagtcc tataacgagc   1080
gcaacccctg ttgttagttg ccagcgagtc aagtcgggaa ctctaacaag actgccagtg   1140
caaactgtga ggaaggtggg gatgacgtca atcatcacg gcccttacgc cttgggctac   1200
```

```
acacgtgcta caatggccgg tacagagagc agccactggg cgaccaggag cgaatctata    1260
aaaccggtca cagttcggat cggagtctgc aactcgactc cgtgaagctg gaatcgctag    1320
taatcggata tcagccatga tccggtgaat acgttcccgg gccttgtaca caccgcccgt    1380
caagccatgg aagctggggg tgcctgaagt cggtgaccgc aaggagctgc ctagggtaaa    1440
actggtaact agggctaagt cgtaacaagg taacc                               1475
```

US 8,956,669 B2

ANTICANCER AND ANTIMICROBIAL COMPOUNDS FROM ANTARCTIC EXTREMOPHILIC MICROORGANSIMS

FIELD OF THE DISCLOSURE

The present disclosure is directed to compounds obtained from extremophilic microorganisms, methods of purifying the same and methods of using the same for treatment and prevention of human disease.

BACKGROUND

Extreme environments offer significant challenges to all life forms existing there. The life forms that do exist in such extreme environments often have unique cellular, physiological and biochemical adaptations that allow them to thrive under conditions in which other life forms would perish. Extremophile microorganisms have been documented to inhabit extreme environments where the physical and chemical parameters have been perceived by humans inhospitable for the existence of known form of life (Pikuta and Hoover, 2000). The dry and cold environment of the Antarctic continent, including lakes and the rest of the pedosphere, offers one example of such an extreme environment.

The study of such extremophile microorganisms has yielded many useful insights to cellular function and has yielded a number of new drugs for study in human disease. Due to the cellular, physiological and biochemical adaptations of these organisms, they offer a unique platform to isolate and identify novel chemical structures for study in the treatment and prevention of human disease.

The present disclosure describes the isolation of "cold loving" psychrotolerant extremophilic microorganisms from the Lakes of Schirmacher Oasis located in the East Antarctic Dronning Maud Land. The isolated organisms were characterized and certain pigments produced by these microorganisms were isolated. The present disclosure teaches that the isolated pigments exhibit anticancer and antimicrobial properties and can be used as new therapies for the treatment and prevention of cancer and microbially mediated diseases.

BRIEF DESCRIPTION OF THE FIGURES

FIG. 3B shows absorption spectrum of the purified yellow/orange pigment from Ant 3-4-2 showing an absorption peak at 450 nm in the visible light range.

FIG. 5A is the 16S rRNA gene sequence from Ant 5-2.

FIG. 5B is the 16S rRNA gene sequence from Ant 3-4-2.

FIG. 8D shows the effect of PVP on induction of apoptosis in murine 2237 fibrosarcoma cells treated with PVP (0 to 1 μM) for 48 hours. Apoptosis was evaluated using the Annexin V-Alexa Fluor488 Apoptosis Vybrant Assay Kit. Annexin V-positive, PI-positive and Annexin V/PI-positive populations were analyzed by flow cytometry. The number of apoptotic cells with or without PVP treatment is shown.

FIG. 9A shows modulation of the expression pattern of proteins of the Bcl-2 family by PVP (0 to 1 μM). After treatments for 48 h, cells were harvested, cell lysates prepared and subjected to Western blotting for Bax and Bcl-2. Equal loading of protein was confirmed by stripping the immunoblot and reprobing it for β-actin.

FIG. 9B shows the change in Bax/Bcl-2 ratio after treatment with PVP (0 to 1 μM) for 48 hours.

FIG. 11A shows the effect of PVP on the viability of A549 human non-small cell lung cancer cell line cells as determined using MTT assay. All data represents the mean±SD of three independent experiments each conducted in triplicate.

FIG. 11B shows the effect of PVP on the viability of MRC-5 normal human lung fibroblasts cells as determined using MTT assay. All data represents the mean±SD of three independent experiments each conducted in triplicate.

DETAILED DESCRIPTION

Figure 1:
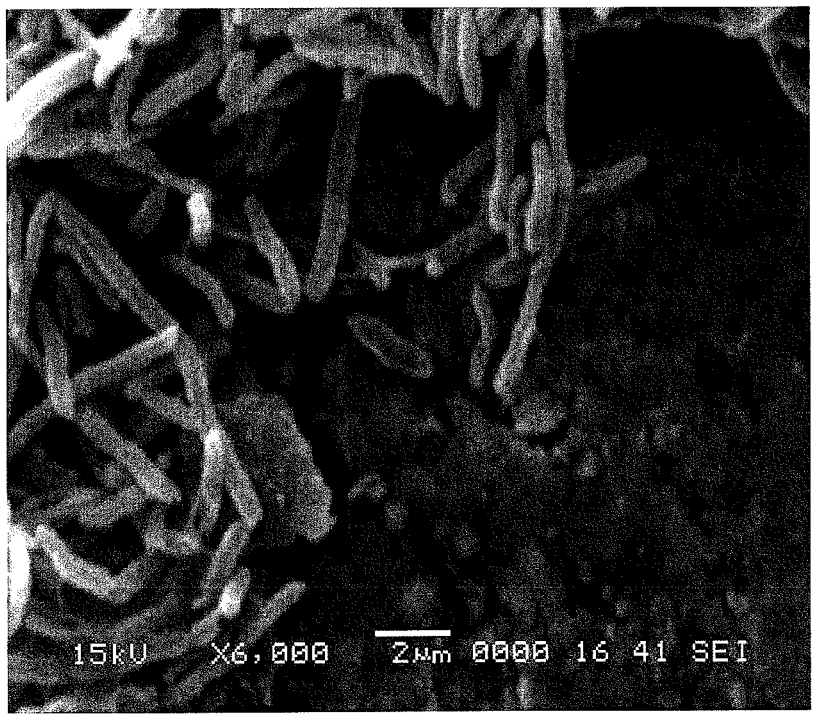
FIG. 1 shows a scanning electron micrograph of a substantially pure culture of Ant 5-2.

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

DEFINITIONS

The terms "prevention", "prevent", "preventing", "suppression", "suppress" and "suppressing" as used herein refer to a course of action (such as administering a compound or pharmaceutical composition) initiated prior to the onset of a symptom, aspect, or characteristics of a disease or condition so as to prevent or reduce such symptom, aspect, or characteristics. Such preventing and suppressing need not be absolute to be useful.

The terms "treatment", "treat" and "treating" as used herein refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristic of a disease or condition. Such effect need not be absolute to be beneficial.

The term "microbial pigment" refers to a colored material of microbial origin, including but not limited to the yellow-orange pigment of Ant 3-4-2 and the purple/violet pigment of Ant 5-2.

The term "pharmaceutically acceptable derivative" means any pharmaceutically acceptable salt, ester, salt of an ester, solvate or other derivative of a microbial pigment of the present disclosure that, upon administration to a subject, is capable of providing (directly or indirectly) the anti-tumor and/or antimicrobial properties of the microbial pigment.

The term "pharmaceutically acceptable salt(s)", unless otherwise indicated, includes salts of acidic or basic groups that may be present in the microbial pigments of the present disclosure.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

The terms "including" and "includes" as used herein are non-exclusive, and can be read to mean "including but not limited to."

The term "halide" as used herein refers to a compound of a halogen with a more electropositive element or radical.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH$(CH_3)_2$, —CH$(CH_3)(CH_2CH_3)$, —CH$(CH_2CH_3)_2$, —C$(CH_3)_3$, —C$(CH_2CH_3)_3$, —CH$_2$CH$(CH_3)_2$, —CH$_2$CH$(CH_3)(CH_2CH_3)$, —CH$_2$CH$(CH_2CH_3)_2$, —CH$_2$C$(CH_3)_3$, —CH$_2$C$(CH_2CH_3)_3$, —CH$(CH_3)$CH$(CH_3)(CH_2CH_3)$, —CH$_2$CH$_2$CH$(CH_3)_2$, —CH$_2$CH$_2$CH$(CH_3)(CH_2CH_3)$, —CH$_2$CH$_2$CH$(CH_2CH_3)_2$, —CH$_2$CH$_2$C$(CH_3)_3$, —CH$_2$CH$_2$C$(CH_2CH_3)_3$, —CH$(CH_3)$CH$_2$CH$(CH_3)_2$, —CH$(CH_3)$CH$(CH_3)$CH$(CH_3)$CH$(CH_3)_2$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl, norbornyl, and bicyclo[2,2,2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. In one embodiment, the unsubstituted alkyl groups include straight and branched chain alkyl groups and cyclic alkyl groups having 1 to 10 or 1 to 5 carbon atoms. In a specific embodiment, the unsubstituted alkyl groups include straight and branched chain alkyl groups having from 1, 2 or 3 carbon atoms.

The phrase "substituted alkyl" refers to an unsubstituted alkyl group as defined above in which one or more bonds to a carbon(s) or hydrogen(s) are replaced by a bond to at least one non-hydrogen and non-carbon atoms such as, but not limited to, a halogen atom in halides such as F, Cl, Br, and I; and oxygen atom in groups such as hydroxyl groups, alkoxy groups, carbonyl groups, carboxyl groups, aryloxy groups, aryloxy groups and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines, hydrazones, and nitriles; a silicon atom in groups such as in trialkylsilyl groups, dialkylarylsilyl groups, alkyldiarylsilyl groups, and triarylsilyl groups; and other heteroatoms in various other groups. In certain embodiments, one or more non-carbon, non-hydrogen atom may be bonded to another non-carbon, non-hydrogen atom, provided that at least one non-carbon, non-hydrogen atom forms a bond to a carbon or hydrogen molecule of the alkyl group. The substituted alkyl group may be bonded to the parent molecule either through the alkyl portion or through the non-carbon/non-hydrogen group. Exemplary substituted alkyl groups include, but are not limited to, —COOH—SO$(CH_2)_m$CH$_3$, CONH$(CH_2)_m$CH$_3$, —N=N$(CH_2)_m$CH$_3$, —N=NO$(CH_2)_m$CH$_3$, N=NNH$(CH_2)_m$CH$_3$, —(SO$_4$)$(CH_2)_m$CH$_3$, —OSOO$(CH_2)_m$CH$_3$, —OSiO$(CH_2)_m$CH$_3$, —OCO$(CH_2)_m$CH$_3$, —CO$(CH_2)_m$CH$_3$, —SO$_2$$(CH_2)_m$CH$_3$, —S$(CH_2)_m$CH$_3$, and —O$(CH_2)_m$CH$_3$, wherein m is 0, 1, 2, 3, 4, 5, 6, 7, 8, 9, or 10. In one embodiment, an exemplary substituted alkyl is —OCH$_3$; the —OCH$_3$ group may be bonded to the parent molecule via the O molecule.

The phrase "unsubstituted alkenyl" refers to straight and branched chain and cyclic groups such as those described with respect to unsubstituted alkyl groups as defined above, except that at least one double bond exists between two carbon atoms.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 member rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 member rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 member rings containing 1 to 2 sulfur atoms and 1 to 3 nitrogen atoms such as, but not limited to, thiazolodinyl; saturated and unsaturated 3 to 8 member rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 member rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 member rings containing an oxygen atom and 1 to 2 sulfur atoms such as, but not limited to, dihydrooxathiinyl; saturated 3 to 8 member rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran. The heterocyclyl group may be bonded to the parent molecule through any portion of the molecule, including the heteroatom portion.

The phrase "substituted heterocyclyl" refers to an unsubstituted heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "unsubstituted heterocyclylalkyl" refers to unsubstituted alkyl groups as defined above in which a hydrogen or carbon bond of the unsubstituted alkyl group is replaced with a bond to a substituted or unsubstituted heterocyclyl group as defined above. For example, methyl (—CH$_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group. The heterocyclylalkyl group may be bonded to the parent molecule through any portion of the molecule, including the alkyl portion or the heterocyclyl portion.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

The phrase "carbocyclic" refers to a ring composed of carbon atoms—used especially of compounds classed as alicyclic or aromatic.

Novel Organisms and Microbial Pigments

A pure culture of an Antarctic extremophile physchrotolerant bacterium has been isolated, designated as Ant 5-2 that is phylogenetically related to *Janthinobacterium* sp. Strain Ant 5-2 produces a purple-violet pigment that is further described below compound (hereinafter "PVP" or "Ant 5-2 pigment"). Another previously unknown organism, strain Ant 3-4-2, produces a yellow/orange pigment (hereinafter "YOP" or "Ant 3-4-2 pigment"), and is phylogenetically related to *Flavobacterium* sp.

It has been unexpectedly discovered that PVP and YOP exhibit anti-cancer activity and anti-bacterial activity. The effectiveness of these pigments bears the potential to be used to develop compositions to treat numerous human diseases, such as cancer and microbially-mediated diseases. These microbial pigments may be used as chemotherapeutic agents and chemo-preventive agents, and as antimicrobial agents.

In a first embodiment, the present disclosure provides for an organism isolated from the water sample of Lake Podprudnoye (Lake P9) in Schirmacher Oasis (S 70° 45' 52.3"-E 11° 37' 10.7") located in the East Antarctic Central Dronning Maud Land (designated strain Ant 5-2). In one embodiment, Ant 5-2 is characterized as having the 16S RNA sequence as shown in SEQ ID NO: 3, or a sequence that is 90, 95, 98 or 99% identical to the sequence as shown in SEQ ID NO: 3. In another embodiment, Ant 5-2 is characterized as having the features recited in Table 1. In still another embodiment, Ant 5-2 is characterized as being a gram negative purple/violet long, round-ended rod approximately. $0.5 \times 2^{-6}$ µm in size.

In a second embodiment, the present disclosure provides for a novel pigment isolated from the organism as described in the first embodiment (designated purple violet pigment or PVP). In one embodiment, the PVP is characterized as having a spectral absorbance at characterized by peaks at wavelengths of 575 nm and of 270 nm. In another embodiment, the PVP is characterized as having a mass spectrum of the following characteristics: large molecular ion 157 m/z (m+1) 344. In a further embodiment, PVP is characterized as being purified by a process described herein. In yet a further embodiment, YOP is characterized as having the structure shown in the general structure III.

In a third embodiment, the present disclosure provides for an organism isolated from a water sample from the land-locked freshwater lake L49 in Schirmacher Oasis (also known as Lake Zub or Lake Priyadarshini) (S 70° 46' 15.2"-E 11° 48' 28.1"), which is located in the East Antarctic Central Dronning Maud Land (designated strain Ant 3-4-2). In one embodiment, Ant 3-4-2 is characterized as having the 16S RNA sequence as shown in SEQ ID NO: 4, or a sequence that is 90, 95, 98 or 99% identical to the sequence as shown in SEQ ID NO: 4. In another embodiment, Ant 3-4-2 is characterized as being a gram negative yellow, thin long filamentous rod.

In a fourth embodiment, the present disclosure provides for a novel pigment isolated from the organism as described in the third embodiment (designated yellow orange pigment or YOP). In one embodiment, the YOP is characterized as having a spectral absorbance at characterized by peaks at a wavelength of 450 nm. In another embodiment, the YOP is characterized as having a mass spectrum of the following characteristics: single major peak of molecular ion at m/z 159 (m+1) 145. In a further embodiment, YOP is characterized as being purified by a process described herein. In still a further embodiment, the YOP is characterized as reacting with 20% KOH by exhibiting an immediate color shift from characteristic yellow or orange to brown. In yet a further embodiment, YOP is characterized as having the structure shown in the general structure I.

In a fifth embodiment, the present disclosure provides for a pharmaceutical composition comprising a compound taught in the second and/or fourth embodiments.

In a sixth embodiment, the present disclosure provides for methods of treating human cancer using a compound of the second and/or fourth embodiments or a pharmaceutical composition of the fifth embodiment. In one embodiment, the cancer is skin cancer, leukemia, breast cancer, colon cancer or lung cancer.

In a seventh embodiment, the present disclosure provides for methods of treating a microbially-mediated disease using a compound of the second and/or fourth embodiments or a pharmaceutical composition of the fifth embodiment. In one embodiment, the disease is caused by a bacterium of the *Mycobacterium* genus, such as *Mycobacterium tuberculosis*.

Isolation and Characterization of Bacterial Strains and Characterization of Pigment Isolation of Strain Ant 5-2

A bacterial strain was isolated from the water sample of Lake Podprudnoye (Lake P9) in Schirmacher Oasis (S 70° 45' 52.3"-E 11° 37' 10.7"), which is located in the East Antarctic Central Dronning Maud Land. The microorganism was grown at 4° C. on R2A agar plates and a pure culture designated as Ant 5-2 was isolated. The composition of R2A agar is well known in the art, and is taught in Ronald M. Atlas (2004) *Handbook of Microbiological Media*, 3rd Ed., CRC Press, which is incorporated herein by reference to teach the preparation of R2A agar and all other microbiological media to which this disclosure refers. Ant 5-2 grows from −1° C. to 37° C. with optimum growth at 22° C.

Ant 5-2 is gram negative purple/violet long, round-ended rod approximately. $0.5 \times 2^{-6}$ µm in size. Ant 5-2 may occur singly, in pairs, sometimes in chains, and occasionally as long filaments. It grows in deep or micro-aerophilic environments. The purity of the culture was determined by Gram stain coupled with microscopy. FIG. 1 shows a scanning electron micrograph of a substantially pure culture of Ant 5-2.

Table 1 provides phenotypic characteristics of Ant 5-2 compared to related, yet distinct, species. From a comparison of the data shown in Table 1, Ant 5-2 is different from the two previously described *Janthinobacterium* species and represents a novel species.

Phylogenetic Analysis of Ant 5-2

Figure 2:
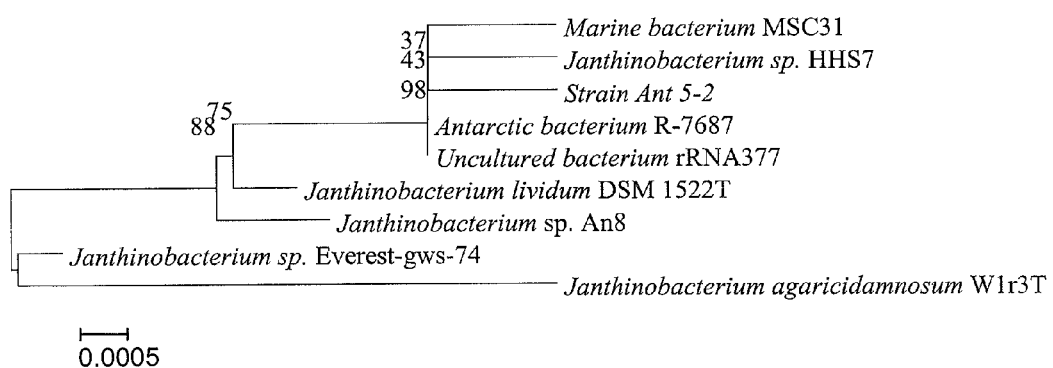
FIG. 2 shows the phylogeny of the 16S rRNA gene of Ant 5-2. Labels on terminal nodes refer to 99% OTU groupings. The tree topology was obtained from neighbor-joining analysis; the numbers on the nodes represent percentage bootstrap support for clades based on 1000 replicates. Scale bar represents 0.5 nucleotide substitutions per site. The OTU was analyzed using BioEdit software and the neighbor-joining phylogenetic analysis was determined using the MEGA 4 software.

The Ant 5-2 isolate was characterized using the standard method of molecular taxonomy of 16S rRNA phylogenetic analysis. A 1.5 kbp conserved segment of the 16S rRNA gene was amplified by polymerase chain reaction ("PCR") using universal eubacterial primers (Garcia-Lopez et al., 2004) F-16S-U8-Lopez 5'-AGAGTTTGATCCTGGCTCAG-3' (SEQ ID NO: 1) and R-16S-U1552-Lopez 5'-AAGGAGG-TAATCCAGCCGCA-3' (SEQ ID NO: 2). The PCR-amplified DNA fragments were cloned in a pGEM-T Easy plasmid vector using the pGEM-T Easy Vector System (Promega) and transformed into JM109 competent cells (Promega). After transformation, randomly selected white colonies were screened for the presence of inserts by colony PCR using the same primers used for amplification. Plasmids were extracted using Qiagen mini-prep columns (Qiagen) from the white colonies containing the inserts. The nucleotide sequences of the cloned gene fragments were analyzed by using M13 forward and reverse primers and an ABI Prism automated DNA sequencer (Perkin Elmer). The 16S rRNA (SEQ ID NO: 3) nucleotide sequences were then compared with the nucleotide sequence database in the NCBI (National Centre for Biotechnology Information) using the BLAST program. The 16S rRNA gene sequence from Ant 5-2 was aligned with homologous sequences obtained from BLAST-P and a phylogenetic tree was established using ClustalW2 and Mega 4 software. On the basis of 16S rRNA gene sequence similarity, strain Ant 5-2 was shown to belong to the β-subclass of Proteobacteria related to *Janthinobacterium lividum* (99%). The results from the phylogenetic analysis are presented in FIG. 2.

Purification and Analysis of PVP from Strain Ant 5-2

Ant 5-2 culture was grown at 22° C. for 4 days in 1:2 (v/v) Trypicase Soy Broth (TSB) medium. A cell pellet was produced from the culture by centrifugation. The cell pellet was then sonicated and PVP was extracted using an equal volume of ethanol twice. The ethanol was then evaporated in a vacuum dryer. It was extracted subsequently with chloroform and diethyl ether to remove cellular debris and deoxyviolacein respectively. Purified dried powder of PVP was obtained.

In an alternative method, PVP was purified by liquid chromatography using a reverse phase flash column (C18 stationary phase; carbon 23%; particle size 40-60 µm, methanol/water (75:25) as mobile phase). The fractions enriched with the pigment were combined and concentrated on a roto-evaporator. The partially purified pigments were further purified by reverse phase HPLC column as described in Rettori, et al. (World J Microbiol Biotechnol. 14, 305 685-688, 1998). After HPLC purification the solvents were removed and the pigment dried on high vacuum pump. The pigment was then analyzed by mass spectra and proton NMR. Mass spectroscopy data was collected using a Micromass Electrospray Ionization Mass Spectrometer and an HP 1100 LC Micromass Platform LCZ with a C18 Column. The concentration of PVP was determined spectrophotometrically.

PVP was diluted in dimethyl sulfoxide (DMSO) for use in further experiments or in ethanol for spectral analysis.

Figure 3A:
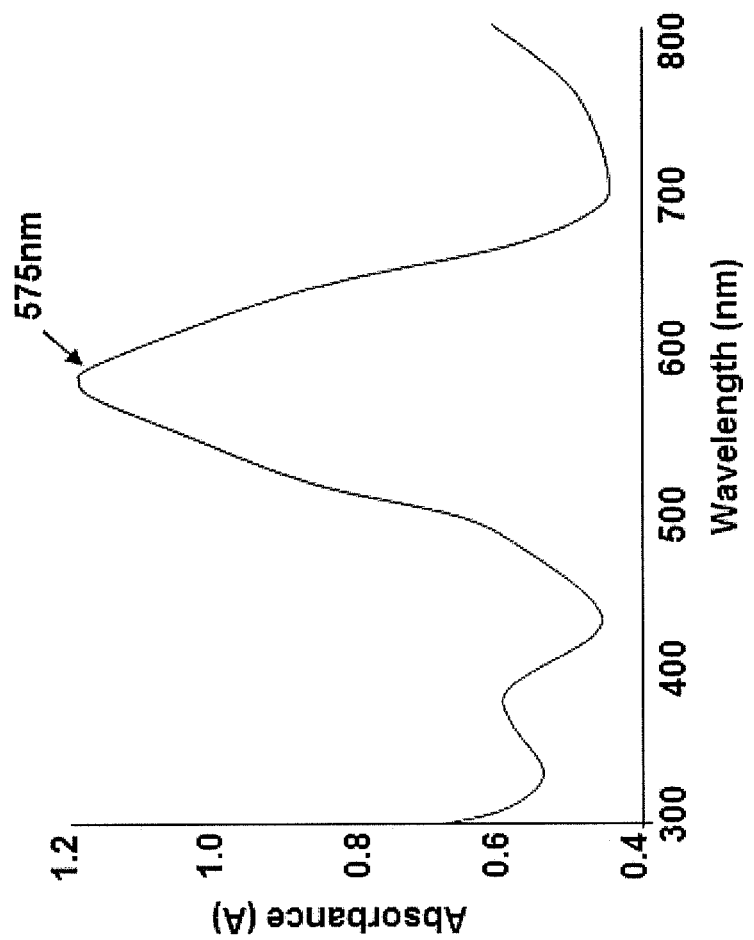
FIG. 3A shows absorption spectrum of the purified purple/violet pigment from Ant 5-2 showing absorption peaks at 575 nm in the visible light range and 270 nm in the uvC range.

Spectral analysis of PVP was performed between the optical range of 200 nm and 720 ran using a Perkin Elmer Lambda 2 spectrophotometer and UV Winlab Lambda 2-40 Version 2.8 software. Results are shown in FIG. 3. The PVP from strain Ant 5-2 exhibits peaks of spectral absorbance at wavelengths of 575 nm and of 270 nm.

Figure 4:
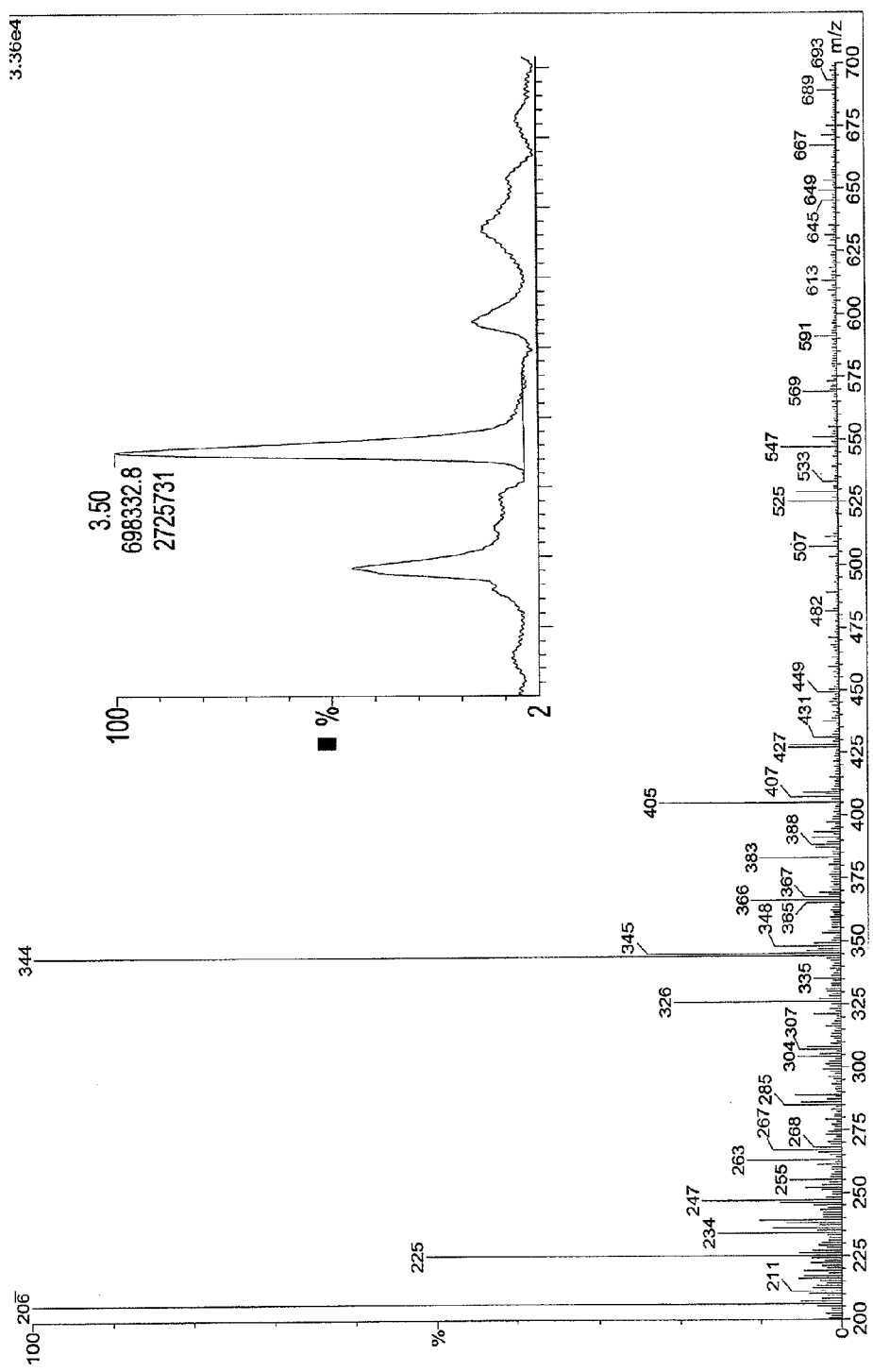
FIG. 4 shows a LC-MS chromatogram showing the peak (ion selected at m/z 344) of the purified purple/violet pigment from Ant 5-2 with the retention time at 3.5 min.

The mass spectrum of the *Janthinobacterium* sp. Ant5-2 showed large molecular ion 157 m/z (m+1) 344 with the retention time at 3.5 min (FIG. 4). The proton NMR also showed the presence of corresponding peaks to the previously reported violacein from *C. violaceum*. In the $^1$H NMR, four $D_2O$ exchangeable protons were observed. Signals at δ 11.93, 10.76, and 10.65 were due to the NH signals and the signal at δ 9.36 can be assigned to the phenolic OH. Similar structures to PVP are known (see above), although unexpectedly the PVP isolated from Ant 5-2 exhibits a higher potency than previously described compounds (data presented below).

The results of DNA-DNA hybridization, physiological and biochemical tests allowed genotypic and phenotypic differentiation of strain Ant5-2 from the only two described *Janthinobacterium* species. Ant5-2 therefore represents a new species, for which the name *Janthinobacterium* sp. nov. is proposed, with the type strain Ant5-2.

Isolation of Strain Ant 3-4-2

A bacterial strain was isolated from a water sample from the land-locked freshwater lake L49 in Schirmacher Oasis (also known as Lake Zub or Lake Priyadarshini) (S 70° 46' 15.2"-E11° 48' 28.1"), which is located in the East Antarctic Central Dronning Maud Land. The microorganism was grown at 4° C. on R2B agar plates and a pure culture designated as Ant 3-4-2 was isolated. Ant 3-4-2 is a gram negative yellow, thin long filamentous rod. The composition of R2B agar is known in the art, and is taught in Ronald M. Atlas (2004) *Handbook of Microbiological Media*, 3rd Ed., CRC Press, which is incorporated herein by reference to teach the preparation of R2B agar. The purity of the culture was determined by Gram stain coupled with microscopy. Ant 3-4-2 was determined to belong to the Flavobacterium family.

Phylogenetic Analysis of Ant 3-4-2

The Ant 3-4-2 isolate was characterized using the standard method of molecular taxonomy of 16S rRNA phylogenetic analysis. Ant 3-4-2 16S rRNA sequence was determined as described above for Ant 5-2. The Ant 3-4-2 16S rRNA sequence is shown in SEQ ID NO: 4. The 16S rRNA gene sequence from Ant 3-4-2 was aligned with homologous sequences obtained from BLAST-P and a phylogenetic tree was established using ClustalW2 and Mega 4 software. On the basis of 16S rRNA gene sequence similarity, strain Ant 3-4-2 was shown to belong to the *Flavobacterium* genus.

Purification and Analysis of YOP from Strain Ant 3-4-2

Ant 3-4-2 pigment was purified by liquid chromatography using a reverse phase flash column (C18 stationary phase; carbon 23%; particle size 40-60 µm, methanol/water (75:25) as mobile phase). The fractions enriched with the pigment were combined and concentrated on a roto-evaporator. The partially purified pigments were further purified by reverse phase HPLC column as described in Rettori, et al. (World J Microbiol Biotechnol. 14, 305 685-688, 1998). After HPLC purification the solvents were removed and the pigment dried on high vacuum pump. YOP was diluted in dimethyl sulfoxide (DMSO) for use in further experiments or in ethanol for spectral analysis.

Spectral analysis of YOP was performed between the optical range of 200 nm and 720 nm using a Perkin Elmer Lambda 2 spectrophotometer and UV Winlab Lambda 2-40 Version 2.8 software. Results are shown in FIG. 3. The YOP from strain Ant 3-4-2 exhibits peaks of spectral absorbance at wavelengths of 450 nm.

Mass spectroscopy data was collected using a Micromass Electrospray Ionization Mass Spectrometer and an HP 1100 LC Micromass Platform LCZ with a C18 Column. The Ant 3-4-2 pigment was treated with 20% KOH to confirm that the pigment is a flexirubin class of pigment (Fautz, E., et al., FEMS Microbiol Lett 8, 87-91, 1980). The concentration of flexirubin was determined by molecular weight. The pigment was diluted in dimethyl sulfoxide (DMSO) for use in further experiments.

The mass spectrum for YOP exhibited a single major peak of molecular ion at m/z 159 (m+1) 145, which is characteristic for the flexirubin class of pigment. The YOP from Ant 3-4-2 exhibited an immediate color shift from characteristic yellow or orange to brown when flooded with 20% KOH and reverted to its initial color when flooded by an acidic solution once the excess KOH was removed (Fautz, E., et al., FEMS Microbiol Lett 8, 87-91, 1980).

Effect of PVP on Skin Cancer

Skin cancer is a growing health problem around the world predominantly with the changes in the environmental conditions like, ozone depletion leading to the chronic exposure of the skin to solar UV radiation. For example, the UVB component of the solar radiation causes cumulative damage of the skin cells resulting into immuno-suppression that leads to skin cancer. It has been reported that exposure to UV radiation increases the risk of both melanoma and non-melanoma skin cancers in humans. Moreover, it has been estimated that ~1.0 million new cases of non-melanoma skin cancers were diagnosed in 2008 in USA alone causing nearly 1000 deaths. Therefore the art is in need of new compounds to treat and/or prevent skin cancer. The present disclosure provides such a compound.

PVP Inhibits the Growth of Skin Cancer Cells

Figure 6:
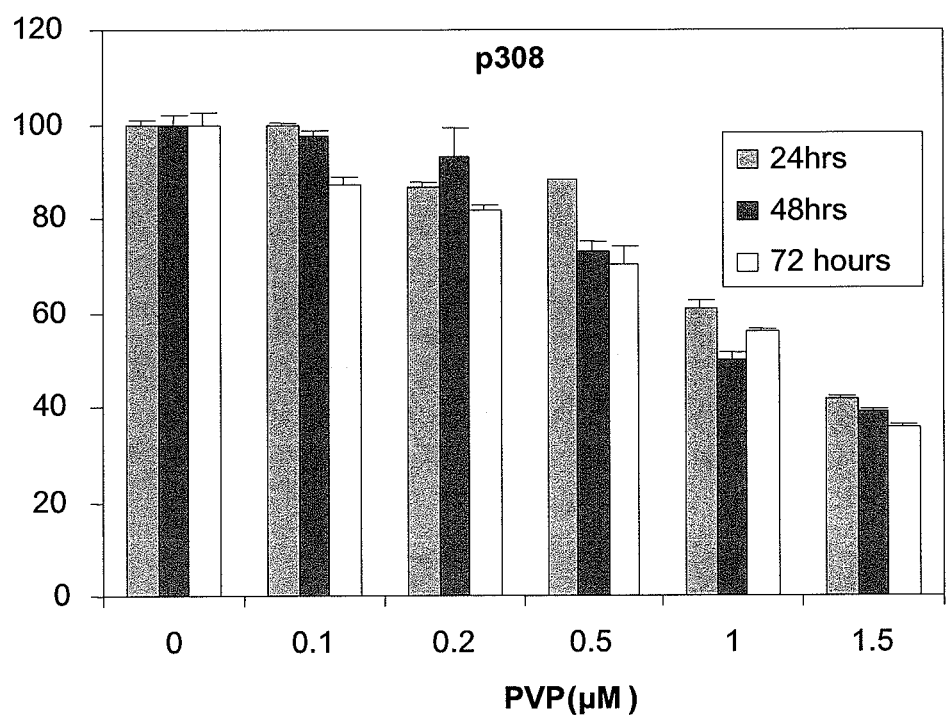
FIG. 6 shows the effect of PVP on the viability of the fibrosarcoma cell line p308 after treatment with purple/violet pigment from Ant 5-2 at 24, 48 and 72 hours as determined by the MTT assay.
Figure 7A:
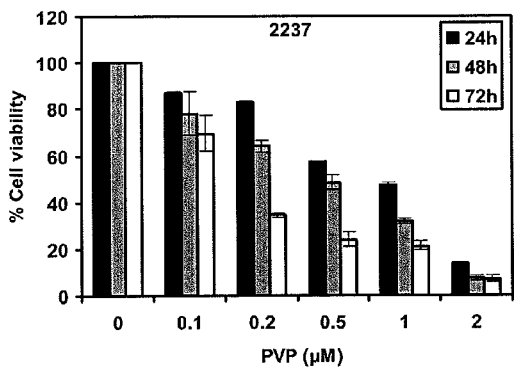
FIG. 7A shows the effect of PVP on the viability of murine 2237 fibrosarcoma cells as determined using MTT assay. All data represents the mean±SD of three independent experiments each conducted in triplicate. Significant difference versus control (0 μM PVP) group are depicted as $*P<0.05$, $**P<0.01$, $¶P<0.001$.
Figure 7B:
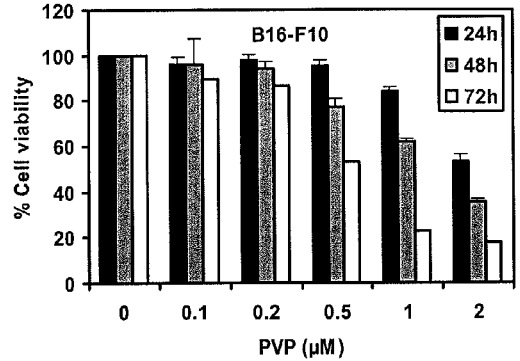
FIG. 7B shows the effect of PVP on the viability of murine B16-F10 melanoma cells as determined using MTT assay. All data represents the mean±SD of three independent experiments each conducted in triplicate. Significant difference versus control (0 μM PVP) group are depicted as $*P<0.05$, $**P<0.01$, $¶P<0.001$.
Figure 7C:
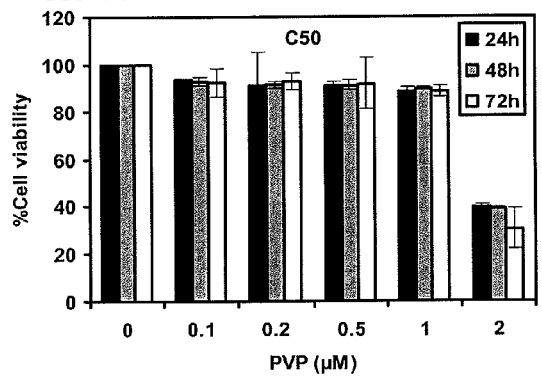
FIG. 7C shows the effect of PVP on the viability of C50 normal keratinocytes as determined using MTT assay. All data represents the mean±SD of three independent experiments each conducted in triplicate. Significant difference versus control (0 μM PVP) group are depicted as $*P<0.05$, $**P<0.01$, $¶P<0.001$.
Figure 7D:
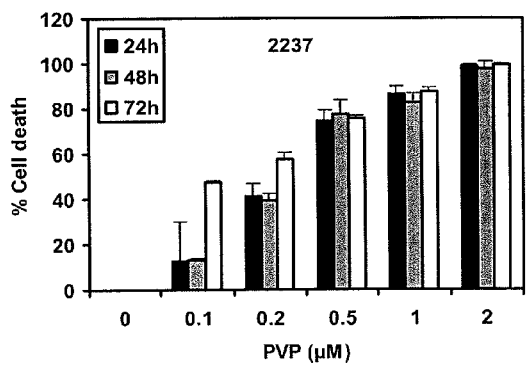
FIG. 7D shows the cytotoxic effect of PVP on murine 2237 fibrosarcoma cell lines as determined using the trypan blue dye exclusion assay and is expressed in terms of percent dead cells. All data represents the mean±SD of three independent experiments each conducted in triplicate. Significant difference versus control (0 μM PVP) group are depicted as $*P<0.05$, $**P<0.01$, $¶P<0.001$.
Figure 7E:
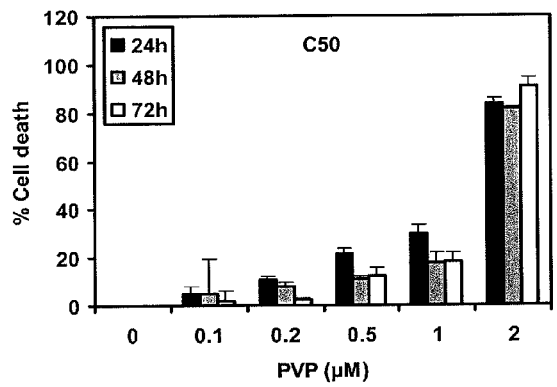
FIG. 7E shows the cytotoxic effect of PVP on C50 normal keratinocytes as determined using the trypan blue dye exclusion assay and is expressed in terms of percent dead cells. All data represents the mean±SD of three independent experiments each conducted in triplicate. Significant difference versus control (0 μM PVP) group are depicted as $*P<0.05$, $**P<0.01$, $¶P<0.001$.

The effect of the PVP on the proliferation capacity of the cells was determined using the MTT assay. As shown in FIG. 5, PVP inhibited proliferation of p308 fibrosarcoma cells in a concentration (0.1-1.5 µM) and time (24-72 hours) dependent manner as determined by the MTT assay. Furthermore, PVP inhibited proliferation of 2237 fibrosarcoma cells in a concentration (0.1-2 µM) and time (24-72 hours) dependent manner as determined by the MTT assay (FIG. 6A) (*P<0.05 to ¶P<0.001). PVP also inhibited proliferation of B16-F10 melanoma cells in a time and concentration-dependent manner as determined by the MTT assay (FIG. 6B) (*P<0.05 to *P<0.01). The effect of PVP on the growth of normal murine keratinocytes C50 cells under identical conditions was also examined. Treatment of the C50 keratinocytes with up to 1 µM PVP showed over 90% viability, as compared to only 20% viability for 2237 fibrosarcoma cells and B16-F10 cells (FIG. 6C).

The results above for 2237 fibrosarcoma cells were confirmed using the Trypan blue assay. Treatment of 2237 fibrosarcoma cells with PVP at similar doses and time interval resulted in significant cell death (up to 99%) (*P<0.05 to ¶P<0.001) (FIG. 6D), whereas the treatment of C50 normal keratinocytes with PVP resulted in cell death of 1.8% to 11% upon treatment of 1 µM PVP for 72 hours (FIG. 6E).

PVP Causes Cell Cycle Arrest, Regulates the Expression of Cell Cycle Proteins and Induces Apoptosis in 2237 Fibrosarcoma Cells In order to investigate the mechanism of PVP inhibition of cellular proliferation in 2237 fibrosarcoma cells, the ability of PVP to induce cell cycle arrest, regulate the expression of cell cycle proteins and induce apoptosis was examined.

Figure 8A:
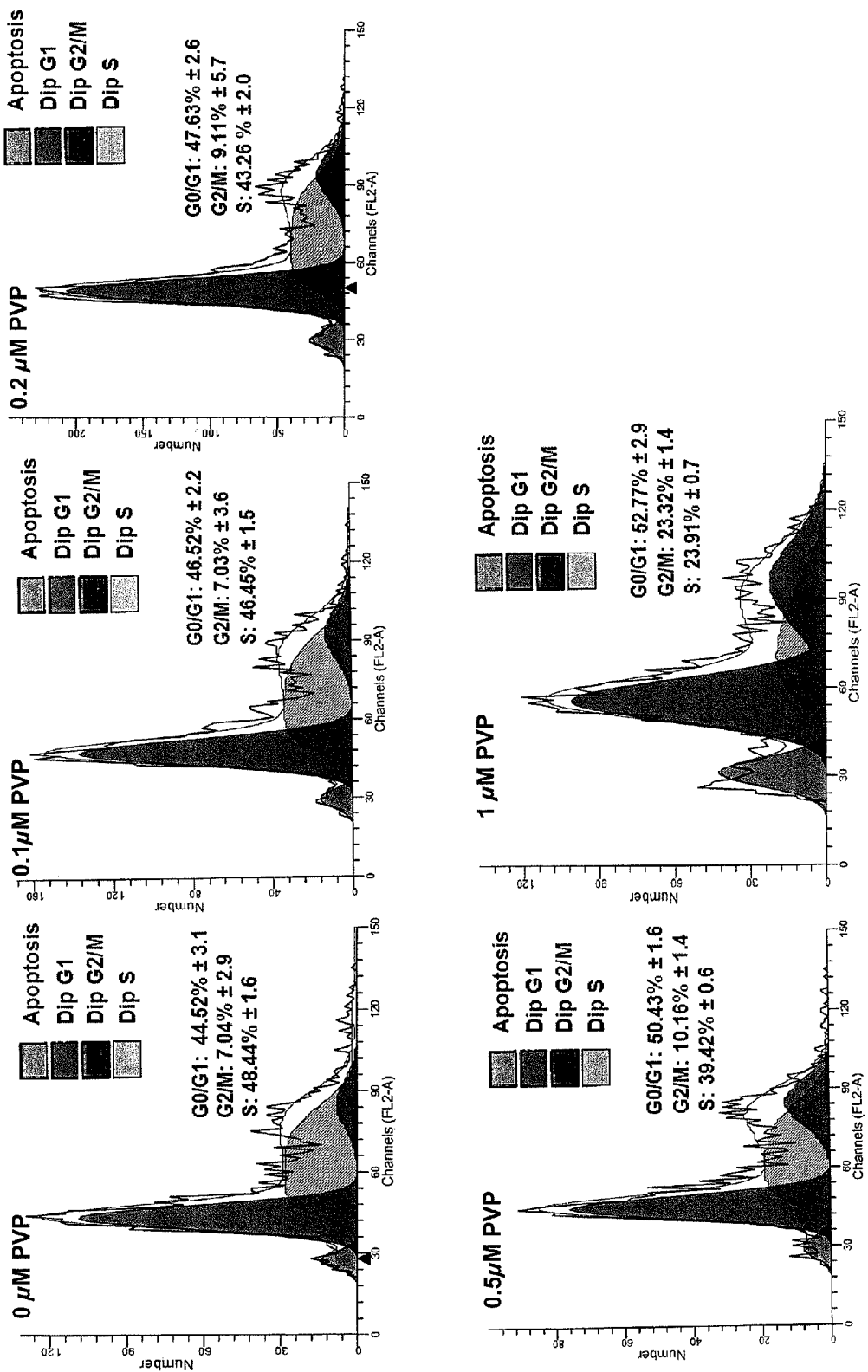
FIG. 8A shows the effect of PVP on the distribution of cells in different phases of cell cycle in murine 2237 fibrosarcoma cells. The cells were treated with PVP (0 to 1 μM) for 24 h and were collected and stained with propidium iodide (PI) followed by flow cytometry analysis. The cellular DNA histograms were further analyzed by Modfit LT. The data are representative example for duplicate tests.

As shown in FIG. 8A, PVP treatment induced a G0/G1 arrest as well as a G2/M phase arrest concomitant with growth inhibitory effects. The distribution of cells in G0/G1 phase was 46.52%, 47.63%, 50.43%, and 52.77% at 0.1, 0.2, 0.5, and 1 µM concentrations of PVP, respectively. The distribution of cells in G2/M phase was 7.03%, 9.11%, 10.16%, and 23.32% at 0.1, 0.2, 0.5, and 1 µM concentrations of PVP, respectively. In addition, there was decrease in cell number during S-phase (48.44% to 23.91%), showing that PVP results in the cell cycle arrest and inhibits the proliferation of murine 2237 fibrosarcoma cells.

Figure 8B:
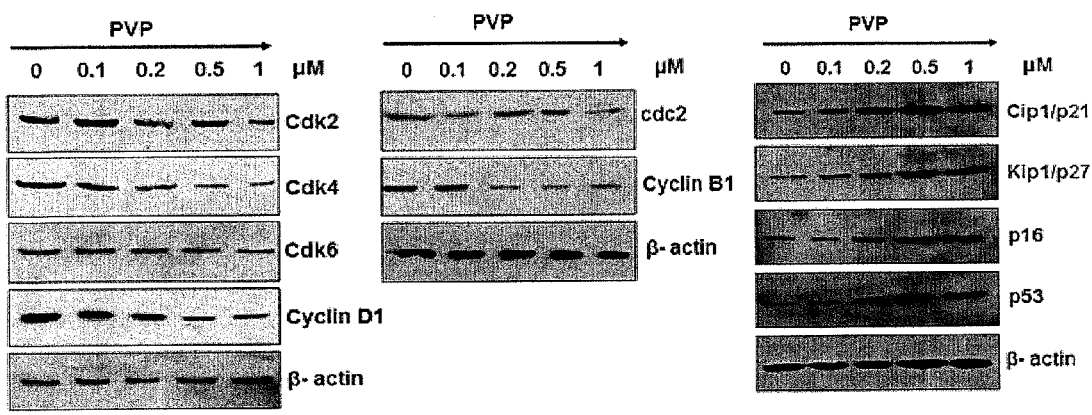
FIG. 8B shows the effect of PVP on the expression of cell cycle regulatory proteins Cdk2, Cdk4, Cdk6, Cyclin D1, Cyclin B1, Cdc2, p21, p27, p16 and p53 in murine 2237 fibrosarcoma cells. The cells were treated with PVP (0 to 1 μM, 48 h) were harvested and cellular lysate was prepared and protein was subjected to SDS-PAGE followed by western blot. Equal loading of protein was confirmed by stripping the immunoblot and reprobing it for β-actin.

To investigate the mechanism underlying the G0/G1 and G2/M arrest, the effect of PVP on cell cycle-regulatory molecules was determined. Immunoblot analysis showed that the PVP treatment resulted in a significant decrease in the protein levels of Cdk 2, Cdk 4, Cdk 6, cyclin D1, cyclin B1 and Cdc2 in a concentration-dependent manner (FIG. X). It was also observed that PVP upregulated the expression of tumor suppressor protein p53 and p16 and its downstream target molecule Kip1/p27, Cip1/p21 (FIG. 8B)

Figure 8C:
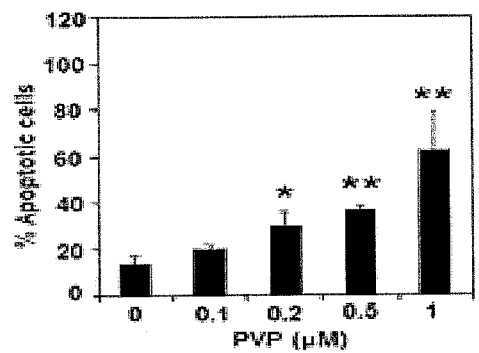
FIG. 8C shows the effect of PVP on induction of apoptosis in murine 2237 fibrosarcoma cells treated with PVP (0 to 1 μM) for 24 hours. Apoptosis was evaluated by staining with Hoechst 33342 (20 μg/ml) and nuclear morphology was observed under a fluorescence microscope. The number of apoptotic cells with or without PVP treatment is shown. The average percentage of apoptotic cells ±SD for each treatment is indicated. $**P<0.01$ vs. control; $*P<0.05$ vs control.

PVP was also demonstrated to induce apoptosis of 2237 fibrosarcoma cells. Staining of 2237 fibrosarcoma cells with Hoechst 33342 dye following treatment with various concentrations of PVP showed a significant increase in apoptosis ranging from 20±2 to 62±17% (*P<0.05, **P<0.01) when compared with controls (DMSO treated 2237 cells) (13±4%) (FIG. 8C). This observation was confirmed by staining PVP treated 2237 fibrosarcoma cells with Annexin-V Alexa fluor 488 and Propidium iodide (PI). Annexin-V specifically binds to phosphatidylserine and has been employed as a useful tool for detecting apoptotic cells. Apoptotic cells (green fluorescence) were found to be increased in PVP treated cells in a dose-dependent manner. Further, Annexin V-positive, PI-positive and Annexin V/PI positive populations were analyzed by flow cytometry (FIG. 8D). PVP treatment induced apoptosis from 26.8% to 78% at increasing concentration (0.1-1 µM).

To further investigate the mechanism of apoptosis in 2237 fibrosarcoma cells, the expression of antiapoptotic and proapoptotic cell regulators was examined. Cells maintain a balance between the concentrations of the antiapoptotic (Bcl-2) and proapoptotic (Bax) proteins. A change in the ratio of these antiapoptotic and proapoptotic cell regulators can suppress or trigger apoptosis. For example, decreased expression of Bcl-2 or increased expression of Bax can be critical for triggering cells to undergo apoptosis. Immunoblot analysis results showed that the PVP treatment of 2237 fibrosarcoma cells increased the expression of Bax with concomitant decrease in the expression of Bcl-2 in a PVP concentration-dependent manner (FIG. 9A). As a result, PVP treatment was found to result in alteration in Bax/Bcl-2 ratio in favor of apoptosis (FIG. 9B).

Figure 9C:
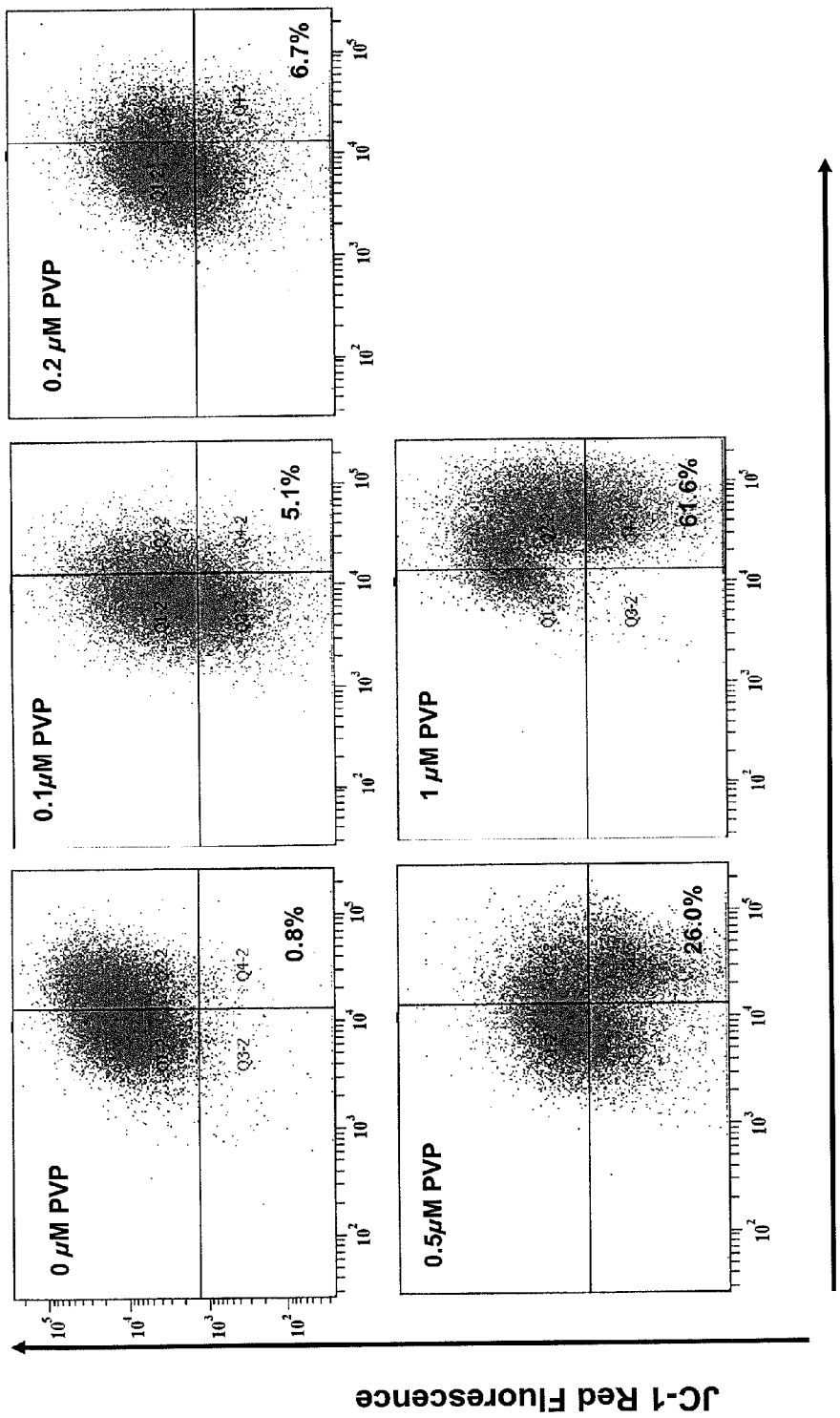
FIG. 9C shows the Effect of PVP on the mitochondrial membrane potential. Treatment of murine 2237 fibrosarcoma cells with PVP (0-1 μM) for 48 hours resulted in the loss of mitochondrial membrane potential in a dose-dependent manner as determined by staining with JC-1 dye and analysis by flow cytometry. The percentage of the cells that emit only green fluorescence indicates the depolarized mitochondrial membrane, as shown in the lower right (LR) quadrant of the FACS histogram.
Figure 9D:
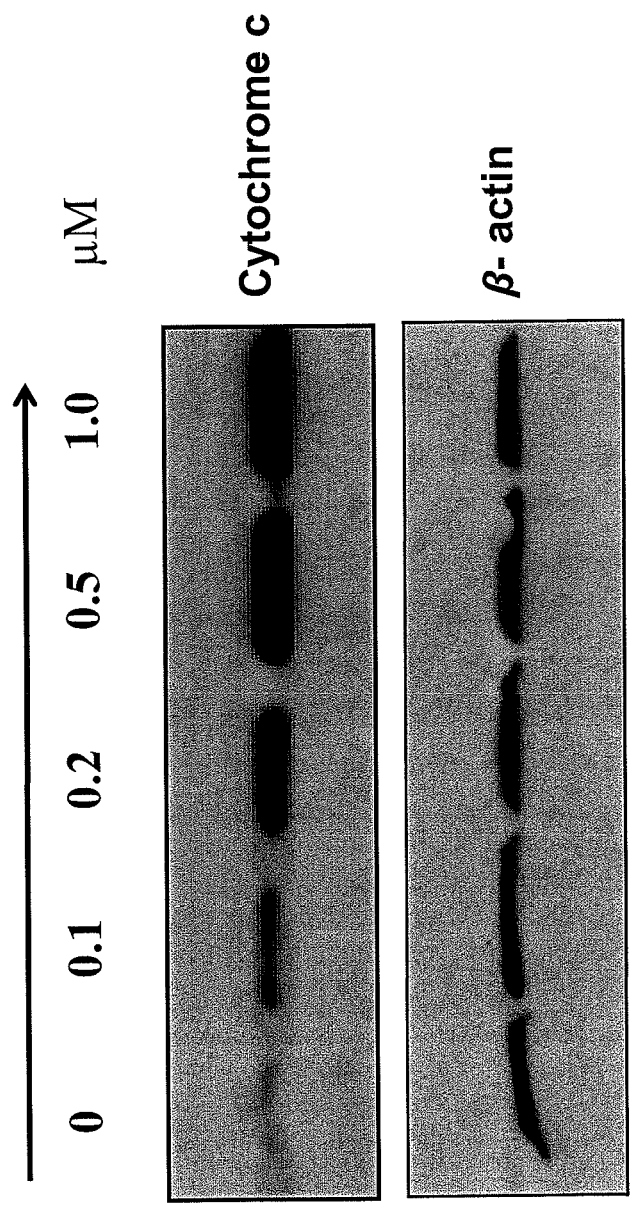
FIG. 9D shows examination of cytosolic fractions were prepared from the same treatment groups as shown in FIG. 9C by Western blot analysis to detect the levels of cytochrome c. Equal loading of protein was confirmed by stripping the immunoblot and reprobing it for β-actin.

One mechanism for the induction of apoptosis is the loss of mitochondrial membrane potential in the cells. The loss of mitochondrial membrane potential is induced by variety of stimuli, including, but not limited to, the translocation of Bax from the cytosol to the mitochondria. The loss of mitochondrial membrane potential triggers the release of cytochrome c from the mitochondria to the cytosol. These events contribute to the activation of caspases and subsequent apoptotic cell death. To investigate the effects of PVP on mitochondrial membrane potential, 2237 fibrosarcoma cells were incubated with the cationic lipophilic dye JC-1 after treatment with PVP. JC-1 dye accumulates within mitochondria in a potential-dependent manner. On disruption of the mitochondrial membrane potential, the fluorescence emission of JC-1 dye changes from red (multimer J-aggregates emitting fluorescence light at 590 nm) to green (monomeric form emits light at 527 nm) after excitation at 490 nm. As shown in FIG. 9C, treatment of 2237 fibrosarcoma cells with PVP resulted in a concentration-dependent increase in the number of cells with green-fluorescence from 0.8% in control treated cells to 5.1, 6.7, 26, and 62.6% at 0.1, 0.2, 0.5 and 1 µM PVP, respectively. Western blot analysis of the cytosolic fractions of the cellular lysates revealed that PVP caused a dose-dependent increase in the release of cytochrome c to the cytoplasm (FIG. 9D), confirming the role of PVP in the disruption of mitochondrial membrane potential.

Figure 10A:
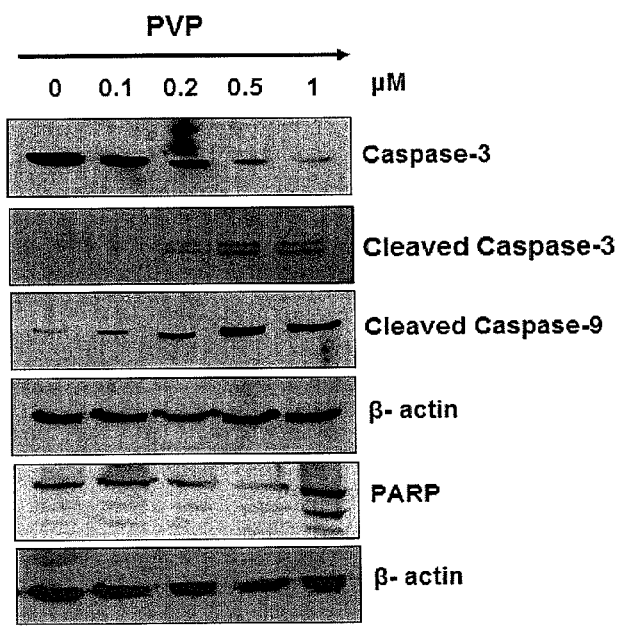
FIG. 10A shows the treatment of murine 2237 fibrosarcoma cells with PVP increases the appearance of cleaved forms of caspase-9, caspase-3 and PARP proteins in a dose-dependent manner. After 48 h of treatment with PVP (0-1 μM), cells were harvested, cell lysates prepared and Western blot analysis was performed to detect the levels of caspase-3, cleaved caspase-9 and -3, and PARP. Equal protein loading was checked by probing stripped blots for β-actin, and a representative blot is shown from two independent experiments with identical observations.
Figure 10B:
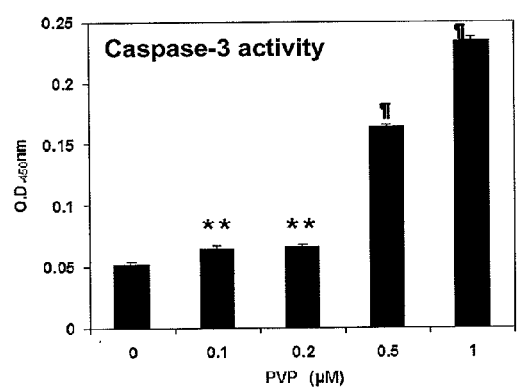
FIG. 10B shows an increase in the activity of caspase-3 after treatment with PVP. Caspase-3 activity was measured in cell lysate samples obtained from the treatment groups of FIG. 10A using the substrate Ac-LEHD-pNA in a colorimetric assay. Data are representative sets from two independent experiments expressed as mean absorbance at 450 nm±SD. Significant difference versus control group is depicted as, *$P<0.05$, ¶$P<0.001$.
Figure 10C:
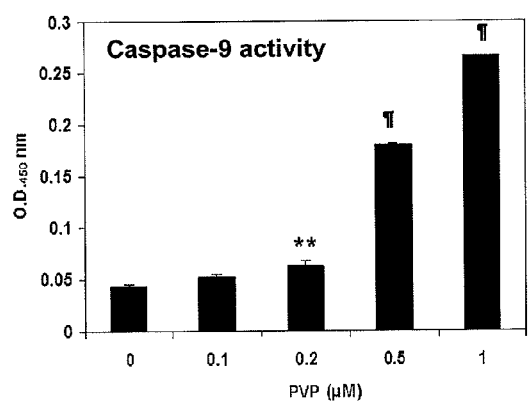
FIG. 10C shows an increase in the activity of caspase-9 after treatment with PVP. Caspase-9 activity was measured in cell lysate samples obtained from the treatment groups of FIG. 10A using the substrate Ac-LEHD-pNA in a colorimetric assay. Data are representative sets from two independent experiments expressed as mean absorbance at 450 nm±SD. Significant difference versus control group is depicted as, *$P<0.05$, ¶$P<0.001$.

PVP also increased the appearance of the cleaved forms of caspase-9 and 3 and increased the activity of caspase-9 and -3 in 2237 fibrosarcoma cells. Western blot analysis using caspase-9 and -3 antibodies showed that PVP treatment decreased the expression of procaspase-3 (a target of caspase-9) and increased expression of cleaved caspase-9 and -3 after 48 hours treatment with PVP (0.1 to 1 µM) (FIG. 10A). The appearance of the cleaved forms of caspase-9 and 3 coincided with the appearance of the cleaved form of PARP (indicated by the presence of 85 and 30 kDa fragments. PARP is a 116 kDa protein that is cleaved during apoptosis and the 85 and 30 kDa fragments serve as a marker for cells undergoing apoptosis and is regarded as hallmark for the induction of apoptotic response. There was marked increase in the amount of 85 kDa fragment in 2237 fibrosarcoma cells treated with 1 µM PVP as compared to control cells (FIG. 10A). The PVP-induced activation of caspase-9 and caspase-3 in 2237 fibrosarcoma cells was further confirmed using a colorimetric caspase-9 and caspase-3 activity assay. Treatment of 2237 fibrosarcoma cells with PVP (0.1 to 1 µM) for 48 h resulted in a significant (**P<0.01, ¶P<0.001) increase in both caspase-3 and caspase-9 activity in a dose-dependent manner as compared to untreated control cells (FIGS. 10B and 10C) confirming the involvement of caspase-9 and -3 activation in apoptotic cell death of 2237 cells.

Materials and Methods

Cell Lines

Murine UV-induced 2237 fibrosarcoma cell line and C50 normal keratinocyte cell line were a kind gift from Dr. Ananthaswamy (Houston, Tex.) and Dr. Susan Fisher (Houston, Tex.) respectively. Murine B16-F10 melanoma cell lines were a kind gift from Dr. Zeng-Bian Zhu (UAB). Murine UV-induced 2237 fibrosarcoma, B16-F10 melanoma and C50 normal keratinocyte cell lines were cultured as monolayer in DMEM supplemented with 10% heat inactivated fetal bovine serum, 100 µg/ml penicillin-streptomycin (Invitrogen, Carlsbad, Calif., USA), and maintained in a humidified atmosphere of 95% air and 5% $CO_2$ at 37° C. PVP in DMSO (0.2% v/v) was used for the treatment of cells. The cells (~70% confluent) were treated either with various concentrations of PVP or DMSO for 24, 48 or 72 h in DMEM medium after which the media was removed and cells were washed with phosphate-buffered saline (PBS, pH 7.4) then harvested by centrifugation.

MTT Assay

The effect of PVP on viability of the cells was determined using MTT assay. The MTT assay is a standard colorimetric assay for measuring the activity of enzymes that reduce 3-(4, 5-Dimethylthiazol-2-yl)-2,5-diphenyltetrazolium bromide (MTT) to purple formazan crystals and is used as a measure of cell viability. Briefly, $5 \times 10^4$ cells/well in 1 ml of complete culture medium was plated in 24-well culture plates. After overnight incubation, the cells were treated with varying concentrations of PVP (0, 0.1, 0.2, 0.5, 1.0 and 2 μM) and further incubated for a 24, 48 and 72 h at 37° C. in a humidified chamber. At the end of the stipulated period, MTT (250 μl of 50 μg/ml stock) was added into each well and incubated for 2 h. The 24-well plate consisting of the cells was centrifuged at 1400 g for 5 min at 4° C. The MTT solution was removed from the wells by aspiration and the resulting formazan was then dissolved in 500 of DMSO and 2000 transferred into a 96 well-plate. The absorbance of the formazan in each well was recorded at 540 nm using a microplate reader (Bio-Rad; Hercules, Calif., USA). The effect of PVP on cell viability was assessed as the percentage of inhibition in cell growth where DMSO-treated cells were taken as 100% viable from three independent experiments.

Cell Death Assay

The trypan blue dye exclusion assay was used to determine the cytotoxic effect of PVP on 2237 fibrosarcoma and C50 cells. Briefly, cells were plated at $5 \times 10^4$ cells in 24-well plates using standard culture conditions as described above. After 24 h, fresh culture medium was added and treated with DMSO as a control or 0.1, 0.2, 0.5, 1 or 2 μM PVP. After 24, 48 or 72 h treatment, cells were collected by a brief trypsinization, and counted in duplicate with a hemocytometer using Trypan blue dye to score dead cells.

Cell Cycle Progression Analysis by Flow Cytometry

The effect of PVP treatment on distribution of cells in different phases of the cell cycle was analyzed by flow cytometry. Briefly, 2237 fibrosarcoma cells were grown in complete culture medium for 24 h. After overnight serum starvation, the cells were treated with DMSO as a control, or 0.1, 0.2, 0.5 or 1 μM PVP. At the end of the desired treatment time, $1 \times 10^6$ cells were collected and resuspended in 50 μl of cold (4° C.) PBS (pH 7.4); cold methanol (450 μl) was added and incubated at 4° C. for 1 h. The cells were centrifuged at 1,400 g for 5 min at 4° C., washed with cold PBS (pH 7.4), re-suspended in 500 μl PBS and incubated with 5 μl RNase (20 μg/ml final concentration) (Ambion, Inc., Austin, Tex.) for 30 min. The cells were incubated with propidium iodide (50 μg/ml final concentration) for 1 h in the dark. The cell cycle distribution of the cells was then determined using a BD FACSCalibur™ Flow Cytometer (BD Biosciences, San Jose, Calif., USA) equipped with BD FACS Diva software. ModFit LT 3.0 cell cycle analysis software was used to determine the percentage of cells in the different phases of cell cycle.

Detection of Apoptotic Cells by Fluorescence Staining (Hoechst 33342)

2237 fibrosarcoma cells were cultured under standard conditions as described above. Cells were treated with DMSO (control) or PVP (0-2 μM) for 24 h. At the end of the incubation period, the cells were trypsinized and washed with PBS (pH 7.4), after which they were cytospinned and fixed in ice cold methanol for 10 min. The cells were then washed twice with PBS and stained with Hoechst 33342 (20 μg/ml) dye for 15 minute in the dark. The morphological changes were observed using an Olympus IX70 (Thornwood, N.Y.) fluorescent microscope at 350 nm excitation light in a blinded manner. The percentage of apoptotic cells was scored by counting at least 3 frames and the average percentage of apoptotic cells was determined for each treatment group.

Apoptosis Assessment by Annexin-V/Propidium Iodide Staining

For the detection of apoptotic and necrotic cells, Vybrant Apoptosis Assay Kit #2 (Molecular Probes Inc., Eugene, Oreg.) was used according to manufacturer's protocol. This kit uses a dual-staining protocol in which the apoptotic cells are stained with annexin-V conjugated Alexa Fluor 488 dye, (green fluorescence), and the necrotic cells are stained with propidium iodide (PI) (red fluorescence). Murine 2237 fibrosarcoma cells were grown to about 70% confluency and treated with DMSO (control) or PVP (0-1 μM) for 48 h. The cells were trypsinized and washed with PBS (pH 7.4) and resuspended in 1× annexin binding buffer. The cells were then incubated with Annexin V Alexa 488 and PI for cellular staining in the dark and cells were either analyzed by FACS using a BD FACSCalibur™ Flow Cytometer equipped with BD FACS Diva software or an Olympus IX70 (Thornwood, N.Y.) fluorescence microscope. Confocal images of green annexin-FITC fluorescence were scored using 488 nm excitation light and images of red PI fluorescence were scored using a 568 nm excitation light.

Preparation of Cell Lysate and Western Blot Analysis

Murine 2237 fibrosarcoma cells were grown and treated with PVP as described earlier. After 48 h, cells were trypsinized and washed with PBS (pH 7.4); homogenized in ice-cold lysis buffer (50 mM Tris-HCl, 150 mM NaCl, 1 mM EGTA, 1 mM EDTA, 20 mM NaF, 100 mM $Na_3VO_4$, 0.5% NP-40, 1% Triton X-100, 1 mM PMSF, pH 7.4) with freshly added protease inhibitor cocktail (Protease Inhibitor Cocktail, Sigma). The homogenate was then centrifuged at 14,000 g for 25 min at 4° C. and the supernatant consisting of the total cell lysate was collected, aliquoted and stored at −80° C. For the preparation of cytosolic fractions, after PVP treatment for 48 h, the medium was aspirated and the cells were washed twice in PBS (pH 7.4). The cells were incubated in 0.2 mL ice-cold lysis buffer (10 mM N-2-hydroxyethylpiperazine-N-2-ethanesulfonic acid [HEPES], 10 mM KCl, 0.1 mM EDTA, 0.1 mM EGTA, 1 mM dithiothreitol [DTT], 1 mM PMSF [pH 7.4]) with freshly added protease inhibitor cocktail for 15 min, after which 12.5 μL of 10% NP-40 was added and the contents were mixed on a vortex and then centrifuged for 1 min (14,000 g) at 4° C. The supernatant was saved as cytosolic lysate and stored at −80° C. The protein content in the lysates was measured by DC Bio-Rad assay (Bio-Rad; Hercules, Calif.) as per the manufacturer's protocol. The proteins (50 μg) were resolved on 10% SDS-polyacrylamide gel and transferred onto nitrocellulose membranes (BioRad). After incubation in blocking buffer (3% Bovine serum albumin in PBS, pH 7.4) for 1 h, the membranes were incubated with the primary antibodies in the blocking buffer overnight at 4° C. The blots were then washed with TBST (Tris-buffered saline-Tween, pH 7.6) and incubated with secondary antibody conjugated with horseradish peroxidase (Thermo-Fisher Scientific). Protein bands were then visualized using the ECL detection system (Amersham Life Science). To verify equal protein loading and transfer of proteins from gel to membrane, the blots were stripped and reprobed for β-actin using an anti-β-actin rabbit polyclonal antibody.

Mitochondrial Membrane Potential Assay

The loss of mitochondrial membrane potential ($\Delta\Psi m$) was quantitatively determined by flow cytometry using the lipophilic cationic probe JC-1 dye (5,5′,6,6′-tetrachloro-1,1′,3,3′-tetraethylbenzimidazolcarbocyanine iodide) (AnaSpec, San Jose, Calif.). Briefly, 70% confluent 2237 cells were treated with DMSO (control) or PVP (0.1, 0.2, 0.5, 1.0 μM) for 48 h, harvested, washed with PBS buffer (pH 7.4) and 1×10⁶ cells were incubated in 1 ml PBS (pH 7.4) consisting of 10 µg JC-1 dye for 15 min at 37° C. in dark. Stained cells were washed, resuspended in 500 µl PBS (pH 7.4) and used for immediate FACS analysis.

Assay for Caspase-3 and Caspase-9 Activity

Caspase-3 and caspase-9 activities were measured in cell lysates by the capacity to cleave their substrates DEVD-pNA and Ac-LEHD-pNA, respectively. Briefly, cultured cells were incubated at 2×10⁶/ml in lysis buffer (50 mM HEPES, 0.1% CHAPS, 1 mM DTT, 0.1 mM EDTA, pH=7.4) for 5 min at 4° C. The cytosolic extracts were collected by centrifugation and the protein concentration was determined using the DC protein assay. Aliquots of 20 µg of the samples were then incubated in the presence caspase-3 and -9 substrates (Biomol, Plymouth Meeting, Pa.) and after 2 h, absorbance was recorded at 450 nm in a Perkin Elmer Lambda II spectrophotometer.

Reagents

Antibodies for β-actin were obtained from Bethyl Laboratories Inc. (Montgomery, Tex.). The Vybrant apoptosis assay kit #2 was purchased from Molecular Probes Inc. Invitrogen (Carlsbad, Calif.). The primary antibodies were purchased as follows: p53, p16, caspase-3, cleaved caspase-9, Bax, Bcl-2, cyclin D1, Cip1/p21, Kip1/p27, Cdk2, Cdk4 and Cdk6 were from Santa Cruz Biotechnology (Santa Cruz, Calif.); cyclinB1 and cytochrome c antibodies for were obtained from eBioscience (San Diego, Calif.); Cdc2 was from BioLegend (San Diego, Calif.); and anti-poly-ADP-ribose-polymerase was from Upstate Cell Signaling Solutions (Lake Placid, N.Y.). The secondary antibodies, horseradish peroxidase-linked anti-mouse immunoglobulin G and anti-rabbit immunoglobulin G, were purchased from Santa Cruz Biotechnology (Santa Cruz, Calif.). The fluorescent dye JC-1 was purchased from AnaSpec (San Jose, Calif.). Caspase-9 substrate and Caspase-3 substrate (chromogenic) were purchased from A.G. Scientific, Inc. (San Diego, Calif.). The DC protein assay kit was obtained from Bio-Rad Laboratories (Hercules, Calif.) and the enhanced chemiluminescence Western blotting detection reagents were purchased from Amersham Pharmacia Biotech (Piscataway, N.J.).

Statistical Analysis

Statistical analysis was performed using one-tailed Student's t-test assuming equal variances and statistical significance is expressed as *$P<0.05$, **$P<0.01$, ¶$P<0.001$. All statistical analyses were conducted using the Microsoft Excel software (Washington, D.C.).

Effect of PVP on Lung Cancer

Lung cancer is the leading cause of cancer-related deaths in the United States. In 2009, 219,440 new cases and 159,390 deaths were estimated from lung cancer (non-small cell and small cell combined) in the United States. It is responsible for more deaths in the United States each year than breast, colon, and prostate cancers combined. One of every three cancer-related deaths is attributable to lung cancer with an overall 5-year survival of 15.7% (Ries et al., 2005). Of the two types of lung cancer i.e. non-small cell lung cancer (NSCLC) and small cell lung cancer, NSCLC represents about 80% of all types of lung cancer and includes squamous cell carcinomas, adenocarcinomas and large cell carcinomas. The current treatment strategies for advanced lung cancer include surgical resection, cytotoxic chemotherapy or chemoradiation therapy (Yang et al., 2005). In almost two-thirds of cases, by the time the cancer is diagnosed, it has already reached to stage of distant metastases (M1) i.e. beyond localized disease limiting therapeutic options (Hoffman et al., 2000; Albain et al., 1991). The art is in need of more effective chemopreventive/chemotherapeutic agents that can be used to treat and/or prevent lung cancer.

The present disclosure shows that PVP inhibits the growth of human lung cancer cells without significantly inhibiting the growth of normal human lung fibroblast cells. Furthermore, the present disclosure shows that PVP increased autophagy in A549 cells.

PVP inhibited the growth of A549 cells in a concentration (0.1-1.0 µM) and time-dependent manner (FIG. 11A). Inhibition of cell growth was observed at almost all concentrations of PVP and time points tested. At 1 µM, PVP inhibited MCF-7 cell growth by 62% at 72 hours. In contrast, PVP showed no significant inhibition of cell growth when tested against the normal human lung fibroblast cell line MRC-5 (FIG. 11B). PVP concentrations from 0.1 to 1 µM failed to demonstrate significant effects on cell growth.

Furthermore, PVP induced autophagy in A549 cells. Autophagy is the process of sequestrating cytoplasmic proteins into the lytic component and is characterized by the formation and promotion of acidic vesicular organelles (AVOs). The vital staining with acridine orange was performed to detect and quantify the AVO in PVP-treated A549 cells. Acridine orange, a lysosomo-tropic agent moves freely across biological membranes when uncharged. Its protonated form accumulates in acidic compartments, where it forms aggregates that fluoresces bright red. Therefore, in acridine orange-stained cells, the cytoplasm and nucleolus fluoresces bright green and dim red, whereas acidic compartments fluoresce bright red. The intensity of the red fluorescence is proportional to the degree of acidity and/or the volume of the cellular acidic compartment. Therefore, a change in the degree of acidity and/or the fractional volume of their cellular acidic compartment can be measured.

Figure 12:
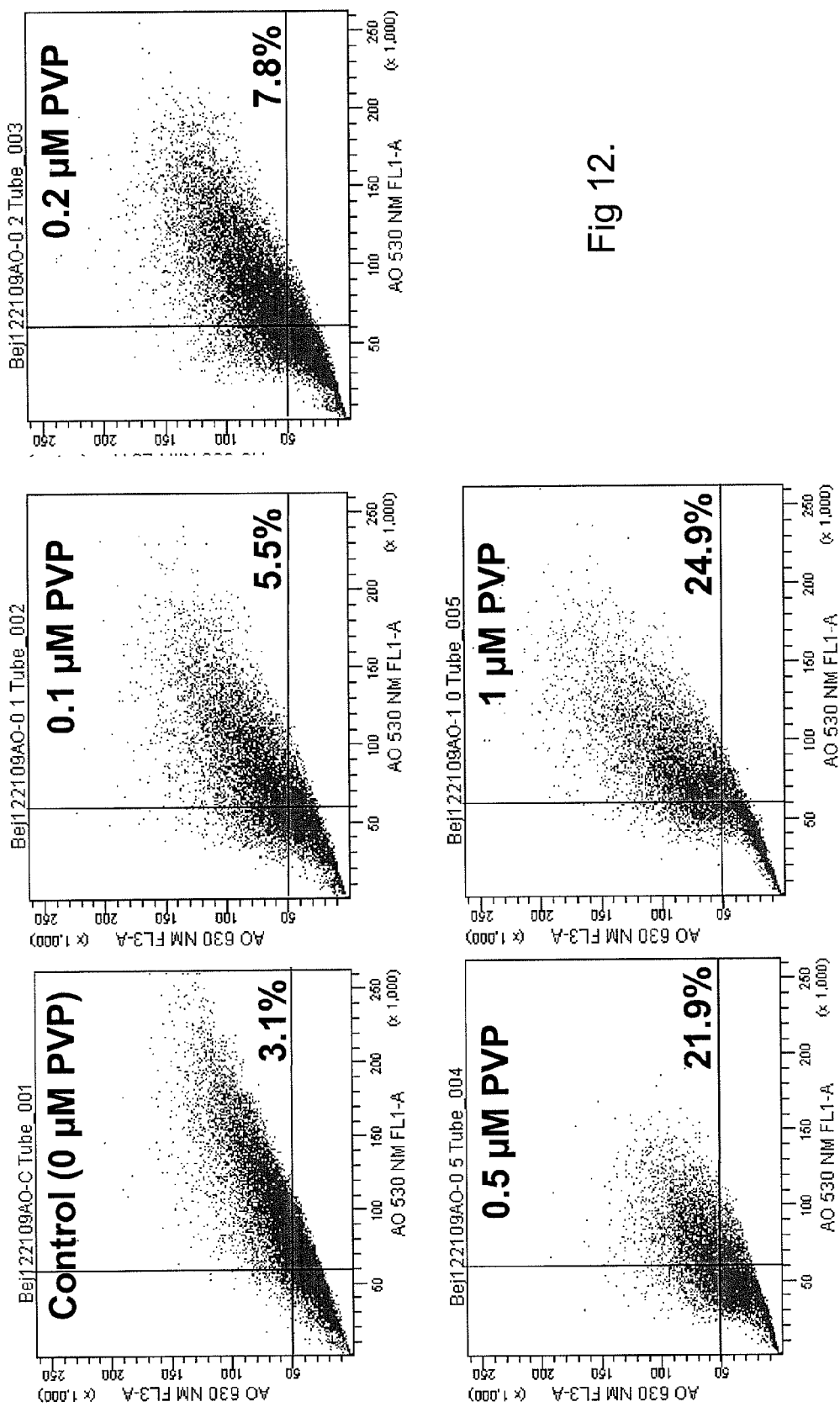
FIG. 12 shows dose dependent acridine orange staining of acidic vesicular organelles (AVO) in human non-small cell lung cancer cell line A549 cells. PVP increased the strength of the bright red fluorescence (y-axis) in A549 cells from 3.1 to 24.9%, indicating development of AVOs.

After 48 hours exposure to PVP (0.1-1.0 µM), cells were stained with acridine orange at a final concentration of 1 mg/ml for 15 min; control cells were treated with DMSO (0.1% as a vehicle control). Green (530 nm) and red (630 nm) fluorescence emission from 30,000 cells illuminated with blue (488 nm) excitation light was measured with a FACS-Calibur from Becton Dickinson using CellQuest™ software. FIG. 12 shows the dose dependent acridine orange staining of acidic vesicular organelles AVO in PVP treated A549 cells. PVP increased the strength of the bright red fluorescence (y-axis) in A549 cells from 3.1 to 24.9%, indicating development of AVOs.

Materials and Methods

Cell Culture

The human non-small cell lung cancer cell line A549 and normal human lung fibroblasts MRC-5 were used in the experiments above. The cells were cultured as monolayers in DMEM medium supplemented with 10% heat inactivated fetal bovine serum, 100 µg/ml penicillin-streptomycin (Invitrogen, Carlsbad, Calif., USA), and maintained in a humidified atmosphere of 5% $CO_2$ at 37° C. PVP in DMSO was used for the treatment of cells.

MTT Assay

The effect of PVP on the proliferation capacity of the cells was determined using MTT assay. Briefly, 5×10³ cells/well were plated in 96-well culture plates. After overnight incubation, the cells were treated with varying concentrations of PVP (0, 0.1, 0.2, 0.5 and 1.0 µM) and the cells incubated for 24, 48 and 72 h. At the end of the stipulated period, MTT (50 µl of 50 µg/ml) was added into each well and incubated for 2 hours. The resulting formazan was then dissolved in 150 µl of dimethyl sulfoxide and the absorbance was recorded at 570 nm using a microplate reader (Dynatech MR5000). The effect of PVP on cell viability was assessed as the percentage of inhibition in cell growth with control cells (treated with DMSO vehicle only) used as 100%.

Effect of PVP on Breast Cancer

Figure 13A:
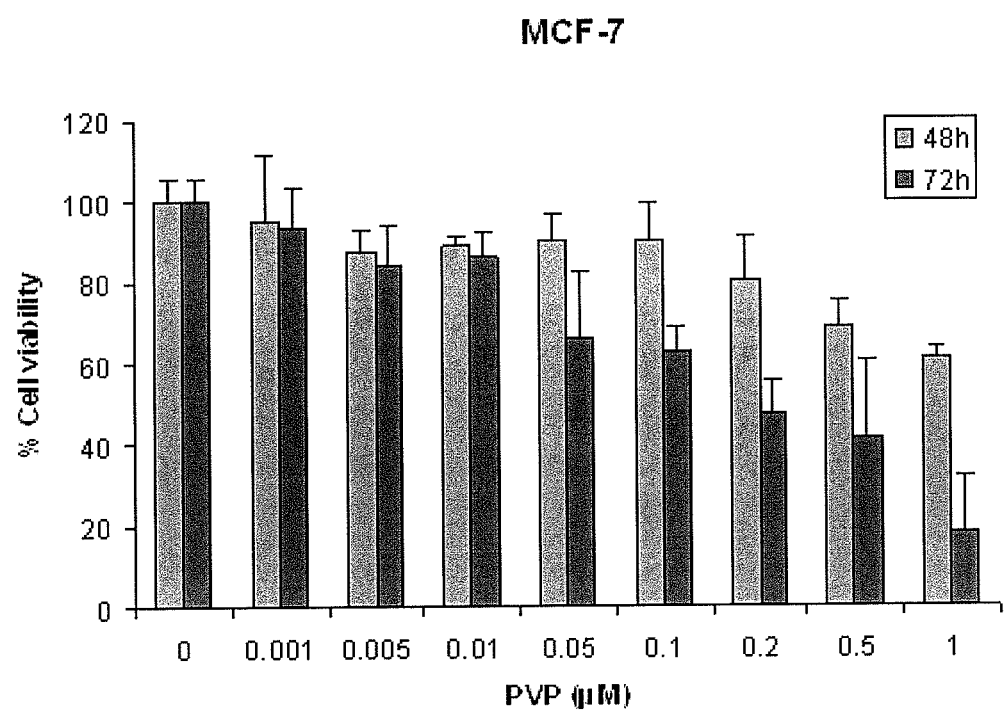
FIG. 13A shows the effect of PVP on the viability of MCF-7 estrogen receptor+human breast cancer cells as determined using MTT assay. All data represents the mean±SD of three independent experiments each conducted in triplicate.
Figure 13B:
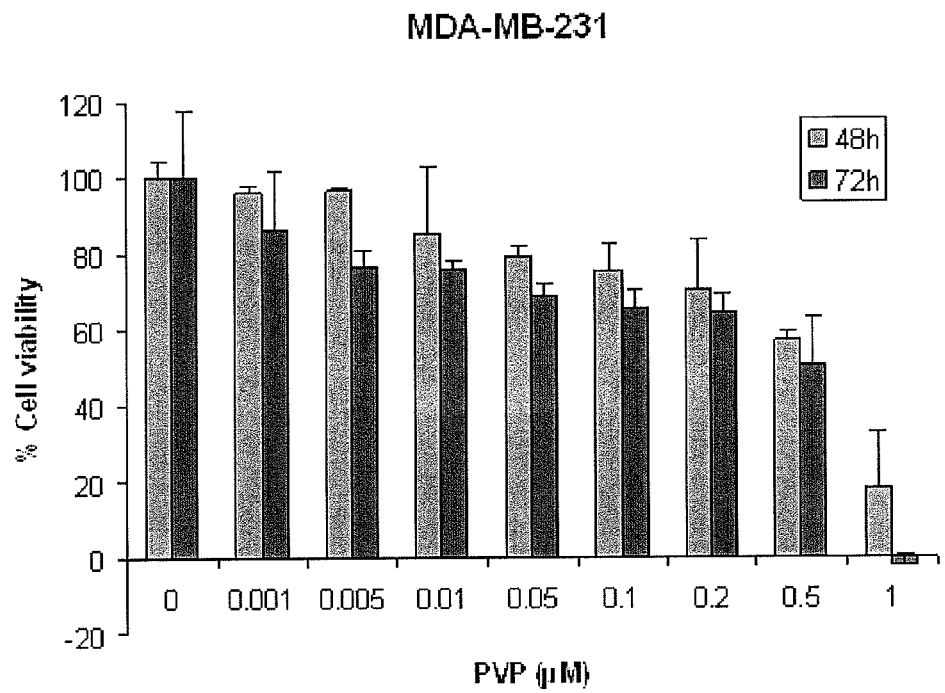
FIG. 13B shows the effect of PVP on the viability of MDA-MB-231 estrogen receptor−human breast cancer cells as determined using MTT assay. All data represents the mean±SD of three independent experiments each conducted in triplicate.

The present disclosure shows that PVP inhibits the growth of human breast cancer cells without significantly inhibiting the growth of normal human breast cancer cells. PVP inhibited the growth of MCF-7 cells in a concentration (0.001-1.0 µM) and time-dependent manner (FIG. 13A). Inhibition of cell growth was observed at all concentrations of PVP tested. At 1 µM, PVP inhibited MCF-7 cell growth by 82% at 72 hours. PVP also inhibited the growth of MDA-MD-231 cells in a concentration (0.001-1.0 µM) and time-dependent manner (FIG. 13B). Inhibition of cell growth was observed at all concentrations of PVP tested. At 1 µM, PVP inhibited MDA-MB-231 cell growth by 100% at 72 hours. The findings above were confirmed visually with microscopic observations.

Figure 13C:
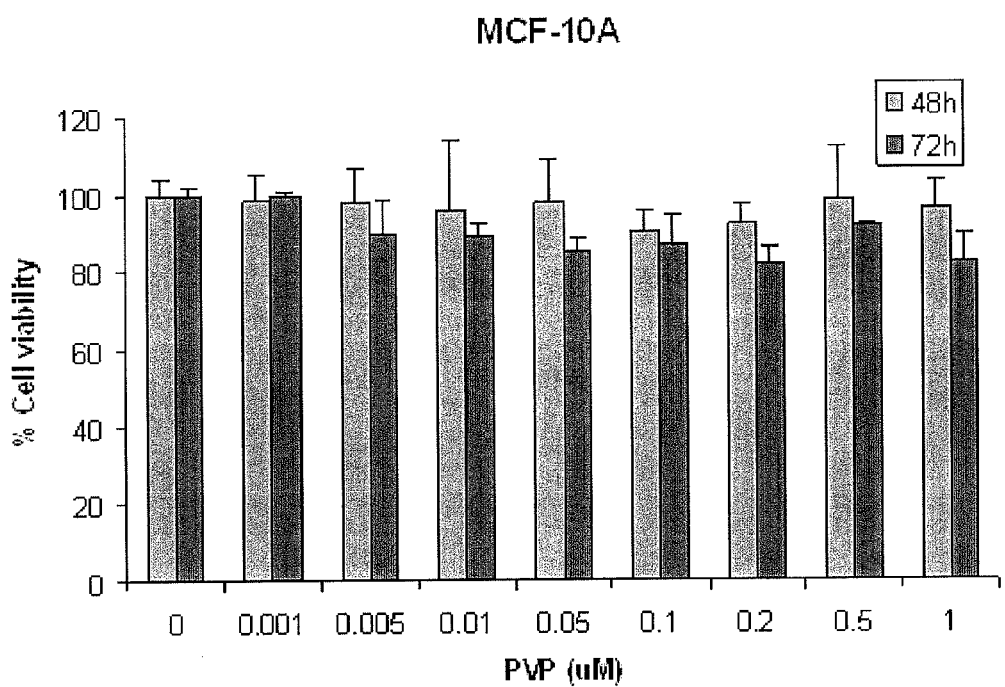
FIG. 13C shows the effect of PVP on the viability of MCF-10A normal human breast cell line as determined using MTT assay. All data represents the mean±SD of three independent experiments each conducted in triplicate.

In contrast, PVP showed no significant inhibition of cell growth when tested against the normal human breast cell line MCF-10A (FIG. 13C). PVP concentrations from 0.001 to 1 µM failed to demonstrate significant effects on cell growth. At 1 µM, PVP reduced proliferation of MCF-10A cells by only 18% after 72 hours incubation. In comparison, PVP inhibited the growth of MCF-7 cells by 82% and inhibited the growth of MDA-MB-231 cells by 100% at the same concentration and time point.

Materials and Methods

Cell Culture

MCF-7 (ER+ human breast cancer cells), MDA-MB-231 (ER– human breast cancer cells) and the normal human breast cell line MCF-10A were used in the experiments described above. The cells were cultured as monolayers in either DMEM or modified 10A media supplemented with 10% heat inactivated fetal bovine serum, 100 µg/ml penicillin-streptomycin (Invitrogen, Carlsbad, Calif., USA), and maintained in a humidified atmosphere of 5% CO at 37° C. PVP in DMSO was used for the treatment of cells.

MTT Assay

The effect of PVP on the proliferation capacity of the cells was determined using MTT assay. The MTT assay was used as described above with the following changes. $1 \times 10^4$ cells/well were plated in 96-well culture plates. After overnight incubation, the cells were treated with varying concentrations of PVP (0, 0.001, 0.005, 0.01, 0.05, 0.1, 0.2, 0.5 and 1.0 µM) and the cells incubated for a further 48 and 72 h.

Effects of PVP and YOP on Mycobacteria

There are over 70 species of Mycobacteria. Of these species, two are major pathogens: *Mycobacterium tuberculosis* (Mtb) and *Mycobacterium leprae*. The remaining mycobacteria are environmental organisms collectively known as MOTTS (mycobacteria other than tuberculosis). In the US, MOTTS are isolated more frequently than *M. tuberculosis* is from clinical specimens. MOTT organisms are responsible for opportunistic infections, especially in people with acquired immune deficiency syndrome (AIDS).

All Mycobacteria are aerobic, contain mycolic acid in their membranes and have a 59-65% GC content in their genomic DNA. Up to 60% of the dry weight of the organisms may be mycolic acids, which are long chain, branched fatty acids. The mycolic acids and short chain fatty acids form a pseudo outer membrane and are responsible for the unusual staining characteristics of the cells and responsible for the hydrophobicity of these organisms. The outer membrane may also be responsible for the development of delayed type hypersensitivity (DTH). All mycobacterial pathogens are intracellular pathogens, with the outer membrane aiding in the survival of the organism by resisting oxidative damage.

*Mycobacterium tuberculosis* (Mtb) is the etiologic agent responsible for causing tuberculosis (TB), resulting into significant morbidity and mortality in humans. *M. tuberculosis* is a slow-growing intracellular pathogen which has a complex cell envelope containing mycolic acid and a diversity of other lipids, many of which are unique to mycobacteria. Tubercle bacilli can remain dormant and therefore viable for many years in the host cells. It is estimated that Mtb has infected more than one third of the world's population and causes the death of about three million people every year, more than any other known pathogenic bacterium. Therefore, TB has been declared a global emergency by World Health Organization. Furthermore, poor treatment compliance selects for multidrug resistant (MDR) strains of Mtb. An even more alarming finding was the recent discovery of extensively drug resistant strains of Mtb (XDR), which are resistant to a number of commonly used effective antituberculosis drugs such as isoniazid and rifampin, fluoroquinolone and at least one of the three injectable drugs capreomycin, kanamycin, and amikacin. The emergence of the XDR strains of Mtb and its rapid worldwide spread has led to the search for a novel antimicrobial agent that could potentially be used to treat patients with infection by this pathogen.

Mycobacteria are also responsible for diseases other than TB. For example, Mycobacteria are responsible for leprosy (Hansen's disease) and Buruli ulcer.

Therefore, novel agents that inhibit the growth and/or viability of *Mycobacterium* sp are needed. The present disclosure shows that PVP and YOP are capable of inhibiting the growth of *Mycobacterium* sp and provides for the use of PVP and YOP in the treatment and prevention of TB and other disease states in which *Mycobacterium* sp play a role.

To test the ability of PVP and YOP to inhibit the growth of *Mycobacterium* sp, two avirulent strains of *Mycobacterium* (*M. smegmatis* $mc^2155$ and *M. tuberculosis* $mc^26230$ (*M. tuberculosis* 91 H37Rv ΔpanCD and ΔRD1)) and a virulent strain *M. tuberculosis*, $H_{37}Rv$ (wild type; ATCC 25618) were used. The *Mycobacterium* strains were treated with PVP and YOP and the minimum inhibitory concentration (MIC) was determined by nitrate reductase assay (NRA) for *M. tuberculosis* $mc^26230$ and *M. tuberculosis* $H_{37}Rv$ or microplate alamar blue assay (MABA) for *M. smegmatis* $mc^2155$ (NRA could not be used for *M. smegmatis* because this bacterium lacks the nitrate reductase enzymes).

MIC for *M. smegmatis* $mc^2155$ Using the MABA Assay

Figure 14A:
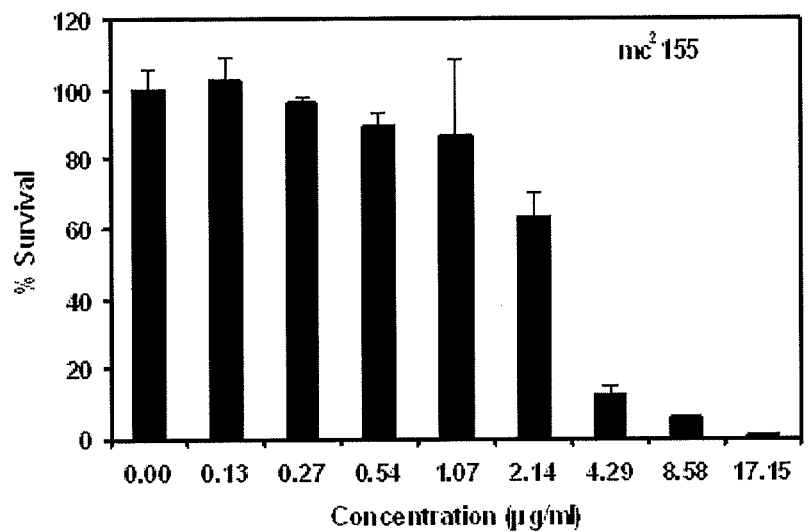
FIG. 14A shows the effect of PVP on the viability of shows the effect of PVP on the viability of *M. smegmatis* mc2155 cells as determined using the microplate alamar blue assay. All data represents the mean±SD of three independent experiments each conducted in triplicate.
Figure 14:
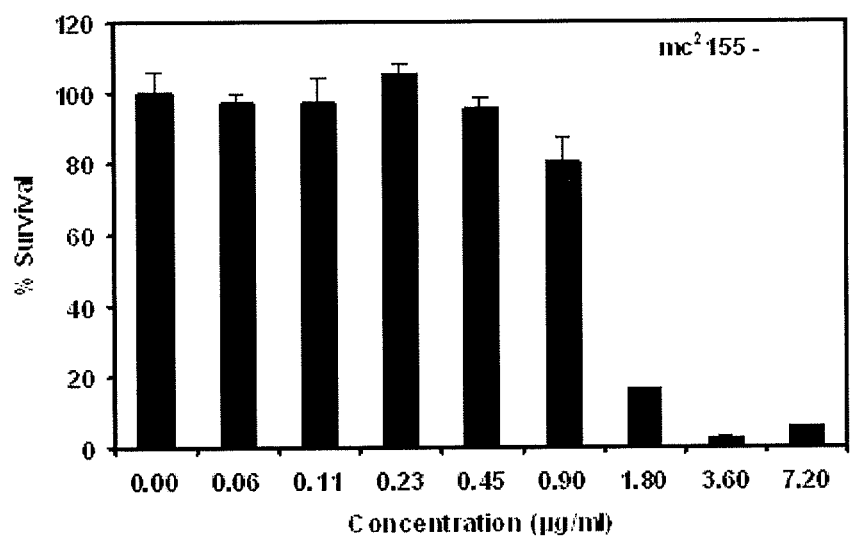
FIG. 14B shows the effect of PVP on the viability of shows the effect of YOP on the viability of *M. smegmatis* mc2155 cells as determined using the microplate alamar blue assay. All data represents the mean±SD of three independent experiments each conducted in triplicate.
FIG. 14C shows the effect of PVP on the viability of shows the effect of PVP on the viability of *M. tuberculosis* mc26230 cells as determined using the nitrate reductase assay. All data represents the mean±SD of three independent experiments each conducted in triplicate.
FIG. 14D shows the effect of YOP on the viability of shows the effect of PVP on the viability of *M. tuberculosis* mc26230 cells as determined using the nitrate reductase assay. All data represents the mean±SD of three independent experiments each conducted in triplicate.
FIG. 14E shows the effect of PVP on the viability of shows the effect of PVP on the viability of *M. tuberculosis* H37Rv cells as determined using the nitrate reductase assay. All data represents the mean±SD of three independent experiments each conducted in triplicate.

The present disclosure shows that PVP extracted from Ant 5-2 and YOP extracted from Ant 3-4-2 inhibited the growth of *M. smegmatis* $mc^2155$. The MIC determined for PVP was 8.6 µg/ml (FIG. 14A) and the MIC determined for YOP was 3.6 µg/ml (FIG. 14B) as determined by MABA. MICs were determined at the concentration that showed <10% survival.

Figure 14C:
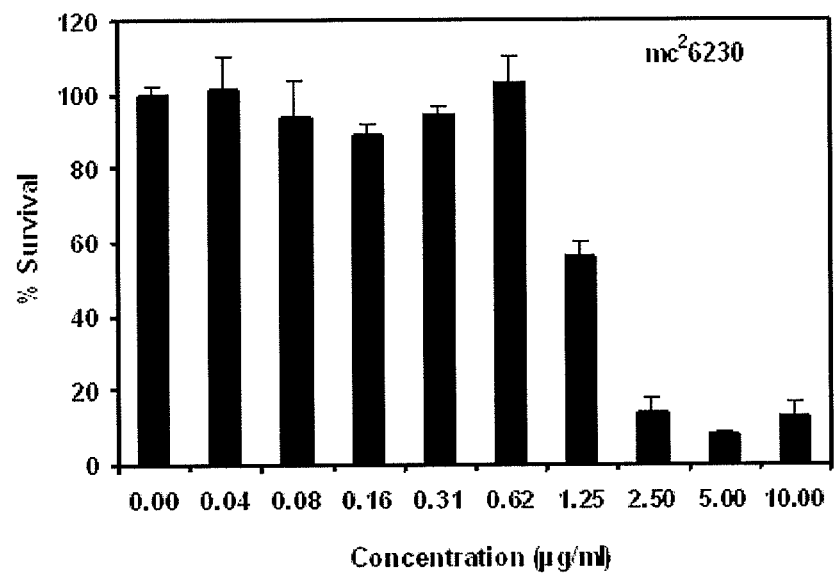
Figure 14D:
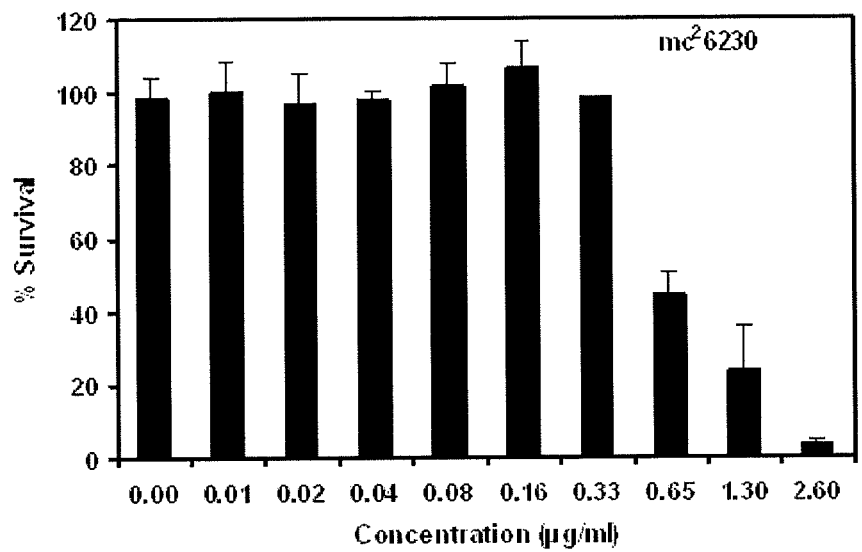

MIC for *M. tuberculosis* $mc^26230$ and *M. tuberculosis* H37Rv Using the NRA Assay The present disclosure shows that PVP extracted from Ant 5-2 and YOP extracted from Ant 3-4-2 inhibited the growth of *M. tuberculosis* mc26230 and *M. tuberculosis* H37Rv. The MIC determined for PVP was 5 µg/ml (FIG. 14C) for *M. tuberculosis* mc26230 and for YOP was 2.6 µg/ml for *M. tuberculosis* $mc_26230$ (FIG. 14D). MICs were determined at the concentration that showed <10% survival for the pigments for *M. tuberculosis* $mc^26230$.

Figure 14E:
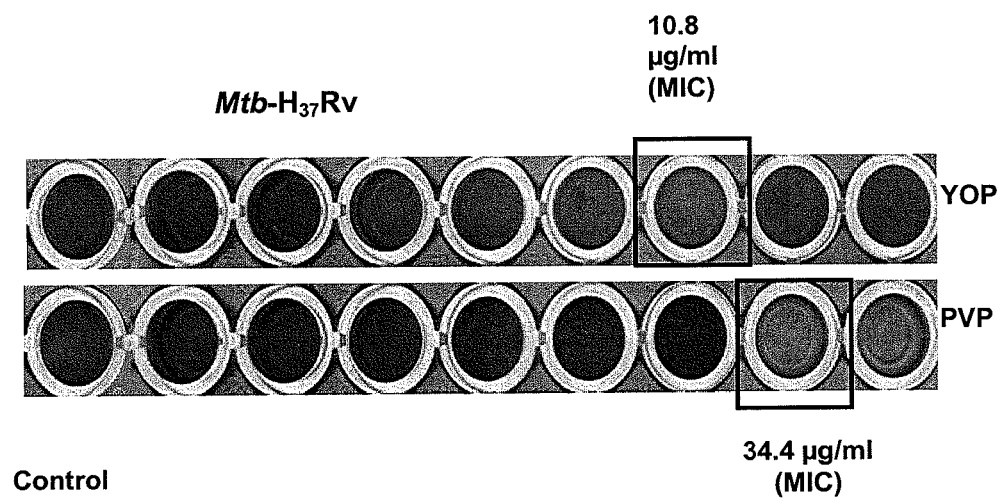

The MIC determined for PVP and YOP for *M. tuberculosis* H37Rv was 34.4 µg/ml and 10.8 µg/ml, respectively. For *M. tuberculosis* H37Rv, the MIC was estimated by visual observation of the color change in the NRA (FIG. 14E).

As summarized in Table 1, the PVP and YOP extracted from Antarctic bacteria Ant-5-2 and ANT 3-4-2, respectively, showed increased efficacy in inhibiting the growth of *Mycobacterium* sp. These pigments were more effective than other plant natural product with the exception of Laburnetin and conventional antibiotics such as Rifampcin, Isoniazid and Ciprofloxacin (Table 1).

Materials and Methods

Cell Culture

*M. smegmatis* mc$^2$155 was grown at 37° C. in Middlebrook 7H9 medium (Difco) supplemented with 0.2% glycerol and 0.05% Tyloxapol (Tx) or on Middlebrook 7H10 Agar (Difco) plates supplemented with 0.5% glycerol. In addition the growth media were supplemented with hygromycin (50 µg/ml) and kanamycin (30 µg/ml) antibiotics. *M. tuberculosis* mc$^2$6230 was grown in Middlebrook 7H9 medium supplemented with 0.2% 97 casamino acids, 24 µg/mL of pantothenate, 0.2% glycerol, 0.05% Tx, and 10% Oleic Albumin Dextrose Catalase (OADC) or on Middlebrook 7H10 agar plates supplemented with 0.2% casamino acids, 24 µg/mL of pantothenate, 0.5% glycerol and 10% OADC. *M. tuberculosis* H37Rv was grown in Middlebrook 7H9 medium supplemented with 0.2% glycerol, 0.05% Tx and 10% OADC or on Middlebrook 7H10 agar plates supplemented with 0.5% glycerol and 10% OADC. Hygromycin B (50 µg/ml) and kanamycin (30 µg/ml) antibiotics were used as necessary.

Nitrate Reductase Assay

*M. tuberculosis* possesses the ability to reduce nitrate to nitrite; this property is routinely used for biochemical identification of mycobacterial species. In the NRA method, the presence of nitrite is detected with specific NRA reagents that produce a color change. The protocol for this commonly used method can be found, for example, in Ängeby et al. (2002) "Rapid and inexpensive drug susceptibility testing of *Mycobacterium tuberculosis* with a nitrate reductase assay" *J. Clinical Microbiology* 40(2): 553-555; and in Kalfin and Engibarov (1989) "Guidelines for microbiological diagnosis of infections caused by mycobacteria," p. 118-127. In M. Stoianova and G. Mitov (ed.), *Handbook of Instructions for Microbiological Diagnosis of Bacterial Infections*, vol. 1, Ministry of Public Health, Sofia, Bulgaria.

For the NRA analysis, bacterial cultures with an $OD_{600}$ of around 1.0 were diluted to 0.04 into standard growth medium supplemented with $NaNO_3$ (1 mg/mL). In a 96 well microtiter plate, 200 µl of sterile Millipore water was added to all perimeter wells and 100 µl of standard liquid media supplemented with $NaNO_3$ was added to all inner wells. Diluted culture (100 µl) was added to each well, which were pre-aliquoted with various concentrations of PVP and YOP. The plates were sealed with aluminum foil and incubated at 37° C. under continuous agitation at 230 rpm. After the incubation period of five days, 50 µl of a reagent mixture consisting of 1 part 50% HCl, 2 parts 0.2% sulphanilic acid, and 2 parts 0.1% 1-napththylamine was added to the samples and absorbance at 570 nm was measured using a microplate reader (Synergy HT microplate reader, Bio-Tek). The results were recorded as negative if there was no color change (indicating a decrease in cell survival), and as positive if there was a color change to pink or to deep red.

Microplate Alamar Blue Assay

Alamar Blue is a redox indicator that yields a colorimetric change and a fluorescent signal in response to metabolic activity. It is a general indicator of cellular growth and/or viability; the blue, non-fluorescent, oxidized form becomes pink and fluorescent upon reduction. Growth can therefore be measured with a fluorometer or spectrophotometer or determined by a visual color change. Methods of using the MABA assay have been developed and successfully used for accurately measuring the MIC of antimicrobial compounds on strains of *Mycobacterium* (see, for example, Collins and Franzblau (1997) "Microplate Alamar Blue assay versus Bactec 460 system for high-throughput screening of compounds against *Mycobacterium tuberculosis* and *Mycobacterium avium*" *Antimicrobial Agents and Chemotherapy* 41(5): 1004).

For MABA, bacterial cultures with an $OD_{600}$ between 0.5-0.9 were diluted to $OD_{600}$ of 0.015-0.02 into standard growth medium. In a 96-well microtiter plate, 200 µl of sterile Millipore water was added to all perimeter wells and 100 µl of standard liquid media was added to all inner wells. Diluted culture (100 µl) was added to each well, which were pre-aliquoted with various concentrations of PVP and YOP. The plates were sealed with aluminum foil and incubated at 37° C. overnight under continuous agitation at 230 rpm. Alamar Blue (40 µl)/5% Tween mixture was added to the wells and re-incubated as before until the drug-free wells turned pink (~3-4 h); fluorescence was measured using a microplate reader (Synergy HT microplate reader, Bio-Tek) at 530/590 nm.

Data Analysis

Data was analyzed using Microsoft Excel software (Microsoft Corp. Seattle, Wash.). Background subtractions using the $OD_{570}$ nm values of the medium controls were performed on all well values. The relative viability/survival [%] was defined as Test well $OD_{570/590}$/Mean pigment-free wells $OD_{570/590 \times 100}$%. The minimum inhibitory concentration (MIC) was set as a 10% relative viability/survival or at 20% relative viability/survival when indicated.

All experiments were conducted in triplicates. Statistical analysis was performed using mean, standard deviation and standard error values of MABA and NRA data from each set of experiment. Each standard error bar indicates standard deviation estimated from 3 independent experiments. Statistical analysis was determined by Microsoft™ Excel 2000 statistical software (Microsoft, Seattle, Wash.).

UV-Radiation Protection

In addition, the pigments described herein are useful in protecting against the impact of solar radiation. The microorganisms disclosed herein inhabit environments with high solar radiation and as a result have developed adaptations to prevent high solar radiation from damaging their nucleic acids.

Solar radiation comprises a spectrum of electromagnetic radiation from 100 to $10^6$ nanometers (nm). This spectrum can be divided into five regions in increasing order of wavelengths Ultraviolet C or (UVC) spans a range of 100 to 280 nm. The term ultraviolet refers to the fact that the radiation is at higher frequency than violet light (and, hence also invisible to the human eye). Owing to absorption by the atmosphere very little reaches the Earth's surface. This spectrum of radiation has germicidal properties, and is used in germicidal lamps. Ultraviolet B or (UVB) range from 280 to 315 nm. It is also greatly absorbed by the atmosphere, and along with UVC is responsible for the photochemical reaction leading to the production of the Ozone layer. Ultraviolet A or (UVA) spans 315 to 400 nm. It has been traditionally held as less damaging to the DNA, and hence used in tanning and PUVA therapy for psoriasis. Visible range or light spans 400 to 700 nm. As the name suggests, it is this range that is visible to the naked eye. Infrared spans 700 nm to $10^6$ nm (1 mm) and is largely responsible for the warmth or heat that the sunlight carries. It is also divided into three types on the basis of wavelength.

Excessive exposure to UV radiation has been linked to all types of skin cancer. One mechanism through which UV exposure causes cancer is via damage to DNA and other nucleic acids. Such damage induces mutations and crosslinking of DNA that can deregulate the normal cellular processes and lead to a cancerous state. The effects of UV radiation can be avoided at least in part through the use of sunscreens to block the UV radiation from reaching the skin. Another detrimental effect of UV exposure is accelerated skin aging (also called skin photodamage), which produces a difficult to treat cosmetic effect. Some people are concerned that ozone depletion is increasing the incidence of such health hazards. A 10% decrease in ozone could cause a 25% increase in skin cancer and accelerated skin aging.

The level of UV light today is higher than it was 50 years ago. This is due to a reduction of ozone in the earth's atmosphere (the Ozone Hole). Ozone serves as a filter to screen out and reduce the amount of UV light that we are exposed to. With less atmospheric ozone, a higher level of UV light reaches the earth's surface. Other influencing factors include elevation, latitude, and cloud cover. UV light is stronger as elevation increases. The thinner atmosphere at higher altitudes cannot filter UV as effectively as it can at sea level. In the Antarctica, Chile, and New Zealand, the UV level is much higher than normal especially in the springtime due to the ozone hole in the southern hemisphere. As a result, it of the increasing exposure to UV light, organisms in the Antarctic region have developed strategies to deal with increased UV exposure.

The pigments described herein play a role in protecting against the damaging effects of solar radiation, in particular UV radiation. As demonstrated in FIG. 3, PVP and YOP exhibit absorption in the UVC, UVB and UVA wavelengths. In one embodiment, the pigment is PVP; in an alternate embodiment, the pigment is YOP.

Methods of Treatment and Prevention

The present disclosure provides compounds for use in the compositions, methods, kits, and other teachings of the instant disclosure. It has been unexpectedly discovered that the PVP isolated from the novel *Janthinobacterium* species designated Ant-5-2 and YOP isolated from the novel *Flavobacterium* species designated Ant 3-4-2 is useful in the treatment and prevention of cancer and bacterial infections.

YOP is a member of the flexirubin family of compounds. The present disclosure describes the uses of members of the flexirubin compounds in the treatment and/or prevention of human disease. The compounds useful in such methods include YOP and those compounds falling under the definition of the general formula I.

Compounds useful in the methods of the present disclosure are defined by the general structural formula (I):

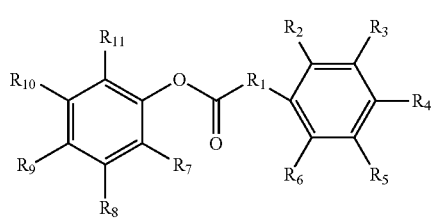

(I)

In this structure $R_1$ represents a substituted or unsubstituted alky or alkenyl group. The substituted or unsubstituted alky or alkenyl group may be of any length. For example, in some embodiments, substituted or unsubstituted alky or alkenyl group comprises 2-32 carbons, any specific value within this range, or any sub-range therein. In one embodiment, the substituted or unsubstituted alky or alkenyl group is an unbranched polyethene. In a specific embodiment the unbranched chain comprises 16 carbons. In a specific embodiment, $R_1$ is a (3E,5E,7E,9E,13E,13E)-hexadeca-1,3,5,7,9,11,13,15-octaene group Groups $R_{2-6}$ may each be independently selected from: —H, —OH, —NH$_2$, —NR$_{12}$R$_{13}$, —COR$_{14}$, —CON=N=N, —N=NR$_{15}$, —N=NOR$_{16}$, —N=NNR$_{17}$, —SR$_{18}$, —SOR$_{19}$, —SO$_2$R$_{20}$, —SO$_3$R$_{21}$, —OR$_{22}$, —XR$_{23}$, —CH$_3$, halogen, alkyl, substituted alkyl, alkenyl, substituted alkenyl, alkynyl, and substituted alkynyl, such that at least one of groups $R_{1-6}$ is selected from the group consisting of —OH, —NH$_2$, —NR$_{12}$R$_{13}$, —COR$_{14}$, —CON=N=N, —N=NR$_{15}$, —N=NOR$_{16}$, —N=NNR$_{17}$, —SR$_{18}$, —SOR$_{19}$, —SO$_2$R$_{20}$, —SO$_3$R$_{21}$, —OR$_{22}$, and —XR$_{23}$; and at least one of groups $R_{1-6}$ is selected from the group —CH$_3$, halogen, alkyl, substituted alkyl, alkenyl, substituted alkenyl, alkynyl, and substituted alkynyl.

In the designations above, the group X is selected from the group consisting of: selenium (Se), tellurium (Te), polonium (Po) and technetium (Tc). The groups $R_{12}$, $R_{13}$, $R_{15}$, $R_{16}$ and $R_{17}$ and $R_{23}$ are each independently selected from the group consisting of: H, OH, alkyl, substituted alkyl, alkenyl, substituted alkenyl, alkynyl, and substituted alkynyl. The groups $R_{14}$, $R_{18}$, $R_{19}$, $R_{20}$ and $R_{21}$ are each independently selected from the group consisting of: H, OH, halogen, unsubstituted alkyl, substituted alkyl, alkenyl, substituted alkenyl, alkynyl, substituted alkynyl, and NR$_{12}$R$_{13}$. The group $R_{22}$ is selected from the group consisting of: H, OH, halogen, unsubstituted alkyl, substituted alkyl, alkenyl, substituted alkenyl, alkynyl, substituted alkynyl COR$_{14}$, and NR$_{12}$R$_{13}$.

In certain embodiments, at least one of groups $R_{2-6}$ is an —OH. In some such embodiments, exactly one of groups $R_{2-6}$ is an —OH, for example $R_4$. In certain embodiments, at least one of groups $R_{2-6}$ is an unsubstituted alkyl group of from 1-6 carbons in length, such as CH$_3$; in some embodiments, exactly one of groups $R_{2-6}$ is an unsubstituted alkyl group of from 1-6 carbons in length, such as CH$_3$, for example $R_3$ or $R_5$. In a particular embodiment of the derivative, $R_4$ is an —OH and $R_3$ is a —CH$_3$.

Groups $R_{7-11}$ may each be independently selected from: —H, —OH, —NH$_2$, —NR$_{12}$R$_{13}$, —COR$_{14}$, —CON=N=N, —N=NR$_{15}$, —N=NOR$_{16}$, —N=NNR$_{17}$, —SR$_{18}$, —SOR$_{19}$, —SO$_2$R$_{20}$, —SO$_3$R$_{21}$, —OR$_{22}$, —XR$_{23}$, —CH$_3$, alkyl, substituted alkyl, alkenyl, substituted alkenyl, alkynyl, and substituted alkynyl, such that at least one of groups $R_{7-11}$ is selected from the group consisting of —OH, —NH$_2$, —NR$_{12}$R$_{13}$, —COR$_{14}$, —CON=N=N, —N=NR$_{15}$, —N=NOR$_{16}$, —N=NNR$_{17}$, —SR$_{18}$, —SOR$_{19}$, —SO$_2$R$_{20}$, —SO$_3$R$_{21}$, —OR$_{22}$, and —XR$_{23}$; and at least one of groups $R_{7-11}$ is selected from —CH$_3$, alkyl, substituted alkyl, alkenyl, substituted alkenyl, alkynyl, and substituted alkynyl. In some embodiments, at least two of groups $R_{7-11}$ are independently selected from —CH$_3$, alkyl, substituted alkyl, alkenyl, substituted alkenyl, alkynyl, and substituted alkynyl.

In certain embodiments of the derivative, at least one of groups $R_{7-11}$ is an —OH. In some such embodiments, exactly one of groups $R_{7-11}$ is an —OH. In a specific embodiment, the —OH is present at positions $R_8$, $R_{10}$ or both. In a particular embodiment $R_{10}$ is an —OH group.

In certain embodiments, at least one of groups $R_{7-11}$ is an unsubstituted alkyl group of from 1-6 carbons in length. In some such embodiments, exactly one of groups $R_{7-11}$ is an unsubstituted alkyl group of from 1-6 carbons in length. In a specific embodiment, the unsubstituted alkyl is a —CH$_3$, and is present at position $R_8$, $R_{10}$, or both. In one embodiment, $R_8$ is —CH$_3$.

In certain embodiments, at least one of groups $R_{7-11}$ is an unsubstituted alkyl group of from 4-23 carbons in length. In some such embodiments, exactly one of groups $R_{7-11}$ is an unsubstituted alkyl group of from 4-23 carbons in length. In some such embodiments the unsubstituted alkyl group is un-branched. In a specific embodiment, the unsubstituted alkyl group comprises 12 carbons and is present at position $R_{11}$.

In a particular embodiment of the derivative, $R_8$ is —$CH_3$, $R_{10}$ is an —OH group, and $R_{11}$ is a dodecyl group.

In one exemplary embodiment of the derivative, $R_1$ is a substituted or unsubstituted alkyl or alkylene group of 2-32 carbons in length, $R_2$ is an —H, $R_3$ is a H, C1-C6 alkyl or halogen (such as —Cl), $R_4$ is an —OH, $R_5$ and $R_6$ are each —H, $R_7$ and $R_9$ are each —H, $R_8$ is a C1-C6 alkyl, $R_{10}$ is an —OH, and $R_1$ is a C4-C23 alkyl. The structure of this compound is presented below:

In an alternate exemplary embodiment of the derivative, $R_1$ is a (3E,5E,7E,9E,11E,13E)-hexadeca-1,3,5,7,9,11,13,15-octaene group, $R_2$ is an —H, $R_3$ is an —$CH_3$, $R_4$ is an —OH, $R_5$ and $R_6$ are each —H, $R_7$ and $R_9$ are each —H, $R_8$ is a —$CH_3$, $R_{10}$ is an —OH, and $R_{11}$ is a dodecane group. The structure of this compound is presented below:

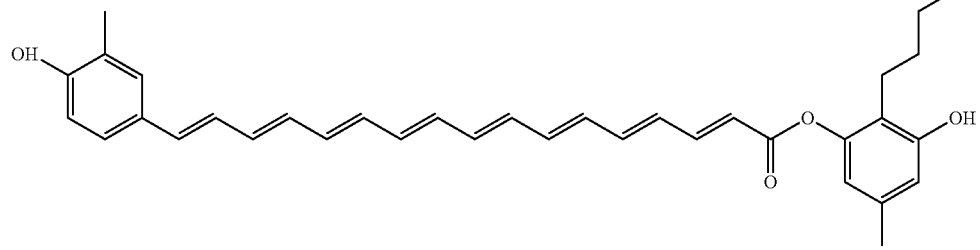

(II)

PVP was purified from a substantially pure culture of Ant 5-2 as described herein. The PVP described in the present disclosure display antimicrobial and antitumor activity. PVP is related to violacein isolated from the bacterium *C. violaceum* but exhibits superior anti-microbial and anti-cancer effects as compared to violacein isolated from the bacterium *C. violaceum*. The violaceins of the present disclosure share a basic structure, based on one of the following core configurations:

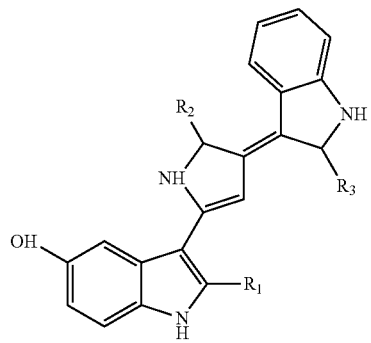

(III a)

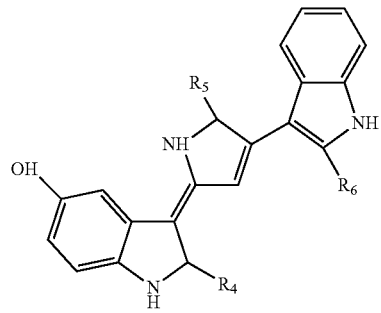

(III b)

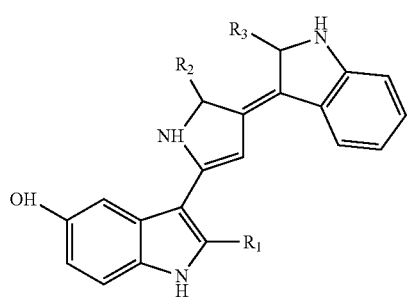

(III c)

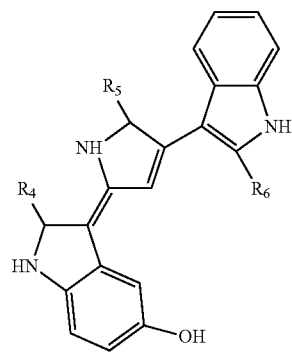

(III d)

The R groups shown have the following identities:

$R_1$ and $R_6$ may be independently selected from —H or a substituted or unsubstituted $C_1$-$C_7$ alkyl or alkenyl group; and $R_{2-5}$ may be independently selected from =O or a substituted or unsubstituted $C_1$-$C_7$ alkyl or alkenyl group.

The foregoing description also includes tautomers of any of the foregoing compounds having the structures shown in III a-d, or a salt thereof. In some embodiments, the PVP of the present disclosure excludes those configurations of (III a) in which all of the following are true: $R_1$ is —H, $R_2$ is =O, and $R_3$ is =O. In some embodiments, $R_1$ and $R_6$ are —H, and $R_{2-5}$ are independently selected from =O or —$CH_3$. In further embodiments, at least one of $R_2$ and $R_3$ is a substituted or unsubstituted $C_1$-$C_7$ alkyl or alkenyl group. In yet a further embodiment, $R_1$ is a substituted or unsubstituted $C_1$-$C_7$ alkyl or alkenyl group. In a particular embodiment, the PVP is based on configuration III c, $R_1$ is —H, $R_2$ is =O, and $R_3$ is =O. In another particular embodiment, the PVP is based on the configuration III b or d and $R_6$ is —H, $R_4$ is =O, and $R_5$ is =O.

In some embodiments, the PVP of the instant disclosure can induce a one-log kill of a subject bacterium (such as a mycobacterium) at a concentration significantly below 60 µg/mL (such a concentration is referred to as a "minimum inhibitory concentration," or "MIC"). Some embodiments of the PVP display an MIC of 11 µg/mL or less. Further embodiments of the PVP display an MIC of 9 µg/mL or less. Still further embodiments of the PVP display an MIC of 5 µg/mL or less.

The present disclosure describes the use of microbial pigments to treat and/or prevent a disease state or condition. In one embodiment, the pigment is PVP isolated as described herein or having the structure shown in III a-d. In one embodiment, the pigment is YOP isolated as described herein or having the structure shown in I. The disease state may be, for example, a cancer. In some embodiments of the method the cancer is a skin cancer, for example a melanoma or a fibrosarcoma. In some embodiments the cancer is a leukemia, breast cancer, colon cancer or lung cancer.

In some embodiments of the method the disease state is a microbially-mediated disease. The disease state may be mediated by a bacterium. The bacterium could be any type of bacterium or pathogenic bacterium. In some embodiments the bacterium is any member of the genus *Mycobacterium*, for example *M. smegmatis, M. tuberculosis, M. bovis, M. africanum, M. microti, M. leprae*, or another pathogenic species of *Mycobacterium* known in the art. In some embodiments of the method the bacterium is any known gram negative pathogenic bacterium, as are known in the art and cataloged in Boone et al. (2001) *Bergey's Manual of Systematic Bacteriology* 2nd Ed., Springer Publishers; by way of example these include species of the genera *Staphylococcus, Vibrio, Escherichia, Salmonella, Shigella* (and other Enterobacteriaceae), *Pseudomonas, Helicobacter, Bdellovibrio, Neisseria, Hemophilus, Proteus, Serratia*, and *Legionella*. In some embodiments the bacterium is a gram-positive pathogenic bacterium, such as *Bacillus, Listeria, Staphylococcus, Streptococcus, Enterococcus, Mycoplasma, Corynebacterium* and *Clostridium*.

In some embodiments of the method the condition is accelerated skin aging, such as that caused by exposure to UV rays. In one embodiment, the UV rays are UVC in an alternate embodiment, the UV rays are UVB; in still another alternate embodiment, the UV rays are UVA; in still a further embodiment, the UV rays are a combination of at least two of UVC, UVB and UVA.

In specific embodiments, the teachings of the present disclosure provide for the treatment of a disease state or condition disclosed herein, such as cancer, a microbially-mediated disease or accelerated skin aging. The methods of treating comprise administering to a subject a compound of the present disclosure. In certain embodiments of the method of treatment, the compound is administered in a therapeutically effective amount. The method of treatment may further comprise identifying a subject in need of such treatment. Such administration thereby treats the disease or condition. When the disease state is a cancer, the treatment of may comprise inhibiting of the proliferation of tumor cells, reducing the viability of the tumor cells or increasing the mortality of the tumor cells (such as by inducing apoptosis). In one embodiment, the cancer is skin cancer, leukemia, breast cancer, colon cancer or lung cancer. When the disease state is a microbially-mediated disease, the treatment may comprise inhibiting the proliferation of the microbial cells, reducing the viability of the microbial cells or increasing the mortality of the microbial cells. In one embodiment, the microbially-mediated disease is caused by a member of the genus *Mycobacterium*, for example *M. smegmatis, M. tuberculosis, M. bovis, M africanum, M microti, M. leprae*, or another pathogenic species of *Mycobacterium* known in the art. As discussed above, the treatment need not be absolute to provide benefit in the treatment methods disclosed.

In specific embodiments, the teachings of the present disclosure provide for the prevention of the disease states and conditions described herein, such as cancer, a microbially-mediated disease or accelerated skin aging. The methods of prevention comprise administering to a subject a compound of the present disclosure. In certain embodiments of the method of prevention, the compound is administered in a therapeutically effective amount. The method of prevention may further comprise identifying a subject in need of such prevention. Such administration would thereby prevent the disease or condition. When the disease state is a cancer, the treatment of may comprise inhibiting of the proliferation of tumor cells, reducing the viability of the tumor cells or increasing the mortality of the tumor cells (such as by inducing apoptosis). In one embodiment, the cancer is skin cancer, leukemia, breast cancer, colon cancer or lung cancer. When the disease state is a microbially-mediated disease, the treatment may comprise inhibiting the proliferation of the microbial cells, reducing the viability of the microbial cells or increasing the mortality of the microbial cells. In one embodiment, the microbially-mediated disease is caused by a member of the genus *Mycobacterium*, for example *M. smegmatis, M. tuberculosis, M. bovis, M. africanum, M. microti, M. leprae*, or another pathogenic species of *Mycobacterium* known in the art. The method of prevention may further comprise identifying a subject in need of such prevention.

The foregoing methods of treatment and/or prevention comprise administering to a subject at least one compound of the present disclosure. The compound may be any of the microbial pigments disclosed herein (such as PVP, YOP, a compound of the general formula 1 or combinations of the foregoing), or a pharmaceutically acceptable derivative thereof. In one embodiment where the disease is cancer, the compound is PVP or a derivative thereof. In one embodiment where the disease is a microbially-mediated disease, the compound is PVP, YOP or a compound of the general formula I.

The compound may be purified or concentrated in some embodiments. In some embodiments the compound comprises a cell that naturally expresses a microbial pigment disclosed herein. The cell may be for example a cell of the strain Ant 5-2 or Ant 3-4-2. In some embodiments of the method the cell that has been genetically modified to express the compound. The cell may be dried, lyophilized, or otherwise preserved in some embodiments.

In some embodiments of the method, the compound is the product of a purification process described herein. For example, the purification process may comprise extracting a cell, such as Ant 5-2 or Ant 3-4-2, with a polar protic extractant to produce a first solution, evaporating the first solution to produce a first evaporite, and extracting the first evaporite with a non-polar or dipolar aprotic extractant. In one embodiment, the polar protic extractant is an alcohol, such as ethanol or methanol and the non-polar or dipolar aprotic extractant is diethyl ether or chloroform, respectively. The process may further comprise second extraction with the polar protic extractant, or additional extractions. The process may further comprise evaporating at least one of the non-polar or dipolar aprotic extractant to produce a second evaporite. The process may further comprise completely evaporating the second evaporite to produce a dried powder. The process may further comprise dissolving the dried powder in a solvent, such as ethanol or dimethyl sulfoxide.

Other extractants and solvents may be substituted for those listed. Such substitutes may be chosen from solvents or extractants with similar indexes of polarity, dipole moment, dielectric constant and miscibility in water to those listed, and such substitutions may be accomplished by those skilled in the art without undue experimentation.

In some embodiments, the process further comprises concentrating a plurality of cells prior to extraction. Concentration may be achieved by any of numerous approaches known in the art, for example sedimenting the cells by centrifugation, collecting the cells by filtration, or concentrating the cells by density-gradient centrifugation. Some embodiments of the method comprise lysing the cells prior to extraction. Lysis of the cells may be achieved by any suitable method known in the art. Sonication of the cells has been found to be particularly suitable. Other lysis methods may include freezing, freezing and thawing, enzymatic lysis (using lysozyme, for example), shearing (using a French press for example), hyperbaric treatment, hypobaric treatment, and osmotic lysis. The cells may be any strain disclosed herein, such as Ant 5-2 or Ant 3-4-2.

In some embodiments of the method, the compound is a component or fraction from strain Ant 5-2 having two spectral absorption local maxima at 270 nm and 575 ran. In further embodiments, the compound is a component or fraction from strain Ant 5-2 having the absorption spectrum as illustrated in FIG. 3, or approximating this absorption spectrum. In further embodiments, the compound is a component or fraction from strain Ant 3-4-2 having the absorption spectrum as illustrated in FIG. 3, or approximating this absorption spectrum.

Compositions

Useful compositions of the present disclosure may comprise one or compounds of the present disclosure useful in the treatment and prevention methods of the present disclosure, such as, but not limited to, those microbial pigments identified in the present disclosure.

In one embodiment, such compositions are pharmaceutical compositions. The compositions disclosed may comprise one or more of such active agents, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). To form a pharmaceutically acceptable composition suitable for administration, such compositions will contain a therapeutically effective amount of an active agent.

The pharmaceutical compositions of the disclosure may be used in the treatment and prevention methods of the present disclosure. Such compositions are administered to a subject in amounts sufficient to deliver a therapeutically effective amount of an active agent so as to be effective in the treatment and prevention methods disclosed herein. The therapeutically effective amount may vary according to a variety of factors such as, but not limited to, the subject's condition, weight, sex and age. Other factors include the mode and site of administration. The pharmaceutical compositions may be provided to the subject in any method known in the art. Exemplary routes of administration include, but are not limited to, subcutaneous, intravenous, topical, epicutaneous, oral, intraosseous, and intramuscular. The compositions of the present disclosure may be administered only one time to the subject or more than one time to the subject. Furthermore, when the compositions are administered to the subject more than once, a variety of regimens may be used, such as, but not limited to, once per day, once per week, once per month, or once per year. The compositions may also be administered to the subject more than one time per day.

The therapeutically effective amount of the active agents and appropriate dosing regimens may be identified by routine testing in order to obtain optimal activity, while minimizing any potential side effects. In addition, co-administration or sequential administration of other agents may be desirable.

For example, in anti-cancer compositions the active agent may be administered in an amount to result in a concentration in the subject of 0.1 µM or above. In some embodiments, the concentration will be 0.2, 0.5, 1 or 1.5 µM or about these amounts. In determining the therapeutically effective amount it should be kept in mind that PVP, for example, reduces the viability of tumor cells in concentrations of 0.1 µM or greater, but also reduces the viability of non-tumor cells at 1.5 µM. In some embodiments in which the active agent comprises PVP, the concentration will be 0.1-1.0 µM, or about these amounts. In some embodiments the concentration will be 0.1 µM to below 1.5 µM or about these amounts. In some embodiments the concentration will be 1 µM or about 1 µM, as this is the estimated IC$_{50}$ of PVP against tumor cells.

In formulating the therapeutically effective amount in treating and preventing microbially-mediated disease, it should be kept in mind that PVP, for example, has a measured MIC of 4.29 mg/L against $M.$ $smegmatis$ and a measured MIC of 2.5 mg/L against $M.$ $tuberculosis$. It should also be kept in mind that YOP has a measured MIC of 20 mg/L against $M.$ $tuberculosis$. In embodiments in which the disease state or condition is mediated by one of these organisms or a related organism, the concentration may be at least about the MIC; the maximum concentration should be formulated keeping in mind that PVP was seen to reduce the viability of normal human cells at 1.5 µM.

The compositions of the present disclosure may be administered systemically, such as by intravenous administration, or locally such as by subcutaneous injection or by application of a paste or cream.

The compositions of the present disclosure may further comprise agents which improve the solubility, half-life, absorption, etc. of the active agents. Furthermore, the compositions of the present disclosure may further comprise other agents that attenuate undesirable side effects and/or or decrease the toxicity of the compounds(s). Examples of such agents are described in a variety of texts, such a, but not limited to, Remington: The Science and Practice of Pharmacy (20$^{th}$ Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In the present disclosure, the pharmaceutical compositions may further comprise a pharmaceutically acceptable carrier including, but not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the compound(s) may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the active agents of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The active agent may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The active agents of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The active agents of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydro gels.

In a particular embodiment, the topical dosage form is a sunscreen. There are two basic types of sunscreen lotions: products that penetrate the outermost layer of skin to absorb ultraviolet rays, and products which coat the surface of the skin to act as physical barriers to ultraviolet rays. Both of these types are rated with a sun protection factor (SPF), which lets the consumer know how much protection against UV rays the product provides. The SPF of a product is the ratio of the time required for a person's protected skin to redden after being exposed to sun-light compared to the time required for the same person's unprotected skin to redden.

Researchers believed that UVB rays, the rays that actually cause a sunburn, were solely responsible for all forms of skin cancer. However, recent studies prove that UVA and UVC rays are also responsible.

Sunscreen compositions are quite often in the form of an emulsion, of oil-in-water type (i.e., a cosmetically and/or dermatologically acceptable carrier consisting of a continuous aqueous dispersing phase and of a discontinuous fatty dispersed phase), or of water-in-oil type (aqueous phase dispersed in a continuous fatty phase), which contains, in varying concentrations, one or more conventional lipophilic organic UV screening agents and/or conventional hydrophilic organic UV screening agents capable of selectively absorbing the harmful UV radiation, these screening agents (and the amounts thereof) being selected as a function of the desired SPF. In such emulsions, the hydrophilic screening agents are present in the aqueous phase and the lipophilic screening agents are present in the fatty phase.

The UV-screening agents most commonly used are organic and soluble in oils or in aqueous media; they generally have, within their structure, a chromophore group linked to a solubilizing group, which is generally a fatty chain in the case of liposoluble UV-screening agents or else a carboxylic or sulfonic acid group in the case of water-soluble UV-screening agents. One screening agent used for protection against UVA rays is avobenzone, or Parsol 1789. Broad spectrum protection is provided by other synthetic ingredients such as benzophenone, oxybenzone, PABA (paraaminobenzoic acid), Padimate-O, a derivative of PABA, homosalate, zinc oxide, octocrylene, octyl methoxycinnamate, octyl salicylate and menthyl anthranilate. Titanium dioxide is a natural mineral and a popular ingredient for broad spectrum protection. Titanium dioxide works by scattering UV light instead of absorbing it. Antioxidants are often combined with titanium dioxide to slow down the oxidation of oils and thereby delay the deterioration of the lotion. Some examples of natural antioxidants are vitamins E and C, rice bran oil and sesame seed oil. Another popular antioxidant in the natural category is green tea. Many newer sunscreen products also contain skin soothing and moisturizing additives such as aloe and chamomile.

The pigments described herein may be added to such sunscreen compositions, either alone or in combination with other ingredients listed above or known in the art, to provide further UV protection. In one embodiment, the pigment is PVP; in an alternate embodiment, the pigment is YOP. Combinations of the foregoing may also be used.

CONCLUSIONS

The foregoing description illustrates and describes the methods and other teachings of the present disclosure. Additionally, the disclosure shows and describes only certain embodiments of the methods and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain best modes known of practicing the methods and other teachings of the present disclosure and to enable others skilled in the art to utilize the teachings of the present disclosure in such, or other, embodiments and with the various modifications required by the particular applications or uses. Accordingly, the methods and other teachings of the present disclosure are not intended to limit the exact embodiments and examples disclosed herein. All references cited herein are incorporated by reference as if fully set forth in this disclosure.

REFERENCES

1. Carmen Veríssima Ferreira, Carina L. Bos, Henri H. Versteeg, Giselle Z. Justo, Nelson Durán and Maikel P. Peppelenbosch. 2004. Molecular mechanism of violacein-mediated human leukemia cell death. *Blood* 104: 1459-1464.
2. Liudmila L. Kodach, Carina L. Bos, Nelson Durá n, Maikel P. Peppelenbosch, Carmen V. Ferreira and James C. H. Hardwick. 2006. Violacein synergistically increases 5-fluorouracil cytotoxicity, induces apoptosis and inhibits Akt-mediated signal transduction in human colorectal cancer cells. *Carcinogenesis* 27:508-516.
3. Nazia Mojib, Richard Hoover and Asim K. Bej. 2008. Diversity and cold adaptation of microorganisms isolated from the Schirmacher Oasis, Antarctica. Proc. of SPIE Vol. 7097 70970K-1.
4. Souza, A. O., Aily, D. C. G., Sato, D. N., and Duran, N. 1999. In vitro Activity of violacein against *Mycobacterium tuberculosis* H37Ra. Rev. Inst. Adolfo Lutz, 58: 59-62.

TABLE 1

| Characteristics | Biochemical tests | Ant5-2 | J. lividum | J. agaricidamnosum |
|---|---|---|---|---|
| Gram reaction | Gram stain, EMB, PEA, MAC | − | − | − |
| Rods | Gram stain | + | + | + |
| Purple pigmentation | Colony morphology | + | + | − |
| Motility | Growth in deep | + | + | + |
| Growth on 2% Nacl | | − | d | + |
| Growth at 4° C. | TSB/R2A agar | + | + | nr |
| Growth at −1° C. | TSB/R2A agar | + | − | − |
| Growth at 37° C. | TSB/R2A agar | + | − | + |
| Anaerobic growth | Growth in deep with mineral oil | + | − | − |
| Nitrate reduction | Nitrate broth | + (complete Reduction) | d | − |
| Production of indole | Indole test | − | − | − |
| Growth on citrate | Citrate test | + | + | + |
| Glucose: | OF Glucose | | | |
| Fermented | and TSI test | + | − | nr |
| Oxidized | | + | + | nr |

TABLE 1-continued

| Characteristics | Biochemical tests | Ant5-2 | J. lividum | J. agaricidamnosum |
|---|---|---|---|---|
| Acid from: | | | | |
| Glucose | Growth media | + | + | + |
| Lactose | | − | + | d |
| Sucrose | | − | + | nr |
| Hydrolysis of: | | | | |
| Starch | Starch agar plate | + | − | nr |
| Gelatin | Gelatin deep | + | + | − |
| Casein | Litmus milk | + | − | − |
| Urease production | Urea broth | − | ? | ? |
| Oxidase | Oxidase test | + | + | + |
| Catalase | Catalase test | + | + | + |
| Reduction of litmus | Litmus milk test | + | nr | nr |
| Acetoin production | VP test | − | nr | nr |
| Stable acid production | Methyl red test | − | nr | nr |
| Lactose fermentation | Mac Conkey Agar plate | − | + | d |
| Acid from: | | | | |
| Dextrose | Fermentation broth | − | nr | nr |
| Growth in: | | | | |
| D-Cellobiose | | − | + | − |
| D-Trehalose | | − | − | + |
| D-Galactose | | − | + | − |
| D-Arabinose | | − | + | − |
| D-Maltose | | − | + | − |
| D-Mannose | | − | + | − |
| D-Melibiose | | − | nr | nr |
| Resistant to: | | | | |
| Ampicillin (25 µg/ml) | | + | d | nr |
| Chloramphenicol (10 µg/ml) | | − | d | nr |
| Tetracycline (10 µg/ml) | | + | − | nr |
| Kanamycin (30 µg/ml) | | + | − | nr |
| Neomycin (10 µg/ml) | | + | − | nr |
| Nalidixic acid (30 µg/ml) | | − | d | − |
| Streptomycin (10 µg/ml) | | + | − | − |
| Ofloxacin (30 µg/ml) | | − | − | nr |
| Amikacin (30 µg/ml) | | + | + | nr |
| Novobiocin (30 µg/ml) | | − | + | nr |
| Coumercin (30 µg/ml) | | + | + | nr |
| Vancomycin (30 µg/ml) | | + | + | + |
| Gentamicin (30 µg/ml) | | + | + | nr |
| Erythromycin (30 µg/ml) | | + | + | nr |
| Rifamicin (30 µg/ml) | | − | + | nr |

TABLE 2

| Compounds | MIC against Mycobacterium smegmatis (µg/ml) | MIC against Mycobacterium tuberculosis (µg/ml) |
|---|---|---|
| Plant phenolic Compounds | | |
| Baicalein | 64[a] | NA |
| Baicalin | 256[a] | NA |
| Biochanin A | 256[a] | NA |
| Daidzein | 256[a] | NA |
| Formononetin | 256[a] | NA |
| Genistein | 256[a] | NA |
| Luteolin | 32[a] | 200[d] |
| Myricetin | 32[a] | NA |
| Resveratrol | 64[a] | NA |
| Chlorpromazine | 64[a] | NA |
| Reserpine | 128[a] | NA |
| Verapamil | 256[a] | NA |
| Laburnetin | NA | 4.88[e] |
| 5,7,2'-trihydroxyflavone | 31[h] | 10[h] |
| Demethoxycurcumin | NA | 200[i] |
| Diospyrin | 100[j] | 100[j] |
| Allicin | NA | 25[k] |
| Diospyrone, crassiflorone and plumbagin | 1.22[l] | 39.06[l] |
| Carvacrol, thymol, p-cymene, 1,8-cineole, limonene, and beta-pinene | NA | 62.5-100[m] |

TABLE 2-continued

| Compounds | MIC against *Mycobacterium smegmatis* (μg/ml) | MIC against *Mycobacterium tuberculosis* (μg/ml) |
|---|---|---|
| Conventional Drugs | | |
| Rifampcin | 1[b] | 0.1[f] |
| Isoniazid | 5[b] | 0.1[f] |
| Ciprofloxacin | 1[c] | 0.5[g] |
| This Study | | |
| Violacecin (*Janthinobacterium* sp. | 8.6 3 | 5 ($H_{37}$Ra), 10.8 ($H_{37}$Rv) |
| Ant5-2) Flexirubin (*Flavobacterium* sp. Ant342) | | 20 ($H_{37}$Ra), 34.4 ($H_{37}$Rv) |

NA—not available
[a]Lechner et al 2008;
[b]Mclean et al. 2002;
[c]Wallace et al 1990;
[d]Suksamrarn et al.2003;
[e]Kuete et al 2008;
[f]Chanwong et al 2007;
[g]Shandil et al 2007;
[h]Mativandlela et al 2008;
[i]Agrawal et al 2008;
[j]Lall and Meyer 2001;
[k]Murthy et al 1997;
[l]Kuete et al 2009;
[m]Bueno-Sanchez et al 2009.

What is claimed:

1. A pigmented extract obtained from the bacterium *Janthinobacterium* designated Ant 5-2, wherein the pigmented extract is obtained by:
   (a) performing an extraction on said bacterium with a polar protic solvent to produce a first extract solution;
   (b) evaporating the first extract solution to produce a first evaporite;
   (c) extracting the first evaporite with a non-polar or dipolar aprotic solvent to produce a second extract solution; and
   (d) evaporating the second extract solution to produce a second evaporite, wherein the second evaporite is the pigmented extract.

2. The extract of claim 1, wherein the polar protic solvent is an alcohol.

3. The extract of claim 1, wherein the alcohol is ethanol or methanol.

4. The extract of claim 1, wherein said non-polar or aprotic dipolar solvent is selected from the group consisting of: diethyl ether, chloroform, and a combination thereof.

* * * * *